United States Patent
Qiu et al.

(10) Patent No.: US 12,297,280 B2
(45) Date of Patent: May 13, 2025

(54) MONOCLONAL ANTIBODIES AGAINST HUMAN INTERLEUKIN-4 RECEPTOR ALPHA, ENCODING NUCLEIC ACIDS THEREOF AND METHOD OF USE THEREOF TO TREAT IL-4 OR IL-4/IL-13-MEDIATED DISEASES

(71) Applicant: QYUNS THERAPEUTICS CO., LTD., Jiangsu (CN)

(72) Inventors: Jiwan Qiu, Jiangsu (CN); Wei Chen, Jiangsu (CN); Zhihua Qiu, Jiangsu (CN); Huaiyao Qiao, Jiangsu (CN); Yiliang Wu, Jiangsu (CN)

(73) Assignee: QYUNS THERAPEUTICS CO., LTD., Jiangsu (CN)

(*) Notice: Subject to any disclaimer, the term of this patent is extended or adjusted under 35 U.S.C. 154(b) by 904 days.

(21) Appl. No.: 17/418,571

(22) PCT Filed: Dec. 25, 2019

(86) PCT No.: PCT/CN2019/128156
§ 371 (c)(1),
(2) Date: Jun. 25, 2021

(87) PCT Pub. No.: WO2020/135471
PCT Pub. Date: Jul. 2, 2020

(65) Prior Publication Data
US 2022/0073631 A1    Mar. 10, 2022

(30) Foreign Application Priority Data
Dec. 25, 2018 (CN) .................. 201811592427.X

(51) Int. Cl.
*C07K 16/28* (2006.01)
(52) U.S. Cl.
CPC ...... *C07K 16/2866* (2013.01); *C07K 2317/24* (2013.01); *C07K 2317/76* (2013.01); *C07K 2317/92* (2013.01)
(58) Field of Classification Search
CPC ............ C07K 16/2866; C07K 2317/24; C07K 2317/76; C07K 2317/92
See application file for complete search history.

(56) References Cited

U.S. PATENT DOCUMENTS

| 2011/0008326 A1 | 1/2011 | Hill et al. |
| 2014/0356372 A1 | 12/2014 | Stahl et al. |

FOREIGN PATENT DOCUMENTS

| CN | 1886426 | 12/2006 |
| CN | 102197052 | 9/2011 |
| CN | 103998053 | 8/2014 |
| CN | 108373505 | 8/2018 |
| CN | 108409860 | 8/2018 |
| EP | 3 211 010 | 8/2017 |
| JP | 2017-527560 | 9/2017 |
| WO | 2005/047331 | 5/2005 |
| WO | 2008/054606 | 5/2008 |
| WO | 2009/081201 | 7/2009 |
| WO | 2010/053751 | 5/2010 |
| WO | 2013/087660 | 6/2013 |
| WO | 2016/034648 | 3/2016 |

OTHER PUBLICATIONS

Ghiasi H, et al. (Oct. 2001) Journal of Virology. 75(19):9029-9036.*
Paludan SR, et al. (1997) FEBS Letters. 414:61-64.*
Zhang M-Z, et al. (2017) Kidney International. 91:375-386.*
Youssef A-R, et al. (2005) Clinical and Experimental Immunology. 139:84-89.*
Supplementary European Search Report issued May 17, 2022, in corresponding European Patent Application No. 19902812.7.
Zaheer Ul-Haq et al., "Interleukin-4 receptor signaling and its binding mechanism: A therapeutic insight from inhibitors tool box", Cytokine & Growth Factor Reviews, vol. 32, 2016, pp. 3-15.
Jung-Eun Kim et al., "Engineering of anti-human interleukin-4 receptor alpha antibodies with potent antagonistic activity", Scientific Reports, vol. 9, 2019, pp. 1-12.
International Search Report issued Mar. 20, 2020 in International (PCT) Application No. PCT/CN2019/128156.
Yang et al., "Construction and panning of scFv phage display library against recombinant interleukin 4 receptor", Chin J Cell Mol Immunol, 2016, vol. 32, Issue 6, pp. 829-833, English abstract.
Kovalenko et al., "Exploratory Population PK Analysis of Dupilumab, a Fully Human Monoclonal Antibody Against IL-4Rα, in Atopic Dermatitis Patients and Normal Volunteers", CPT Pharmacometrics Syst. Pharmacol., 2016, vol. 5, pp. 617-624.

* cited by examiner

*Primary Examiner* — Robert S Landsman
(74) *Attorney, Agent, or Firm* — Wenderoth, Lind & Ponack, L.L.P.

(57) ABSTRACT

Provided are antibodies and fragments against human interleukin-4 receptor alpha (hIL-4Rα) and uses thereof. The antibodies and fragments preferably have heavy chain complementary determining regions as set forth in SEQ ID NOs: 1-3 or 14-16 and light chain complementary determining regions as set forth in SEQ ID NOs: 4-6 or 17-19.

14 Claims, 15 Drawing Sheets
Specification includes a Sequence Listing.

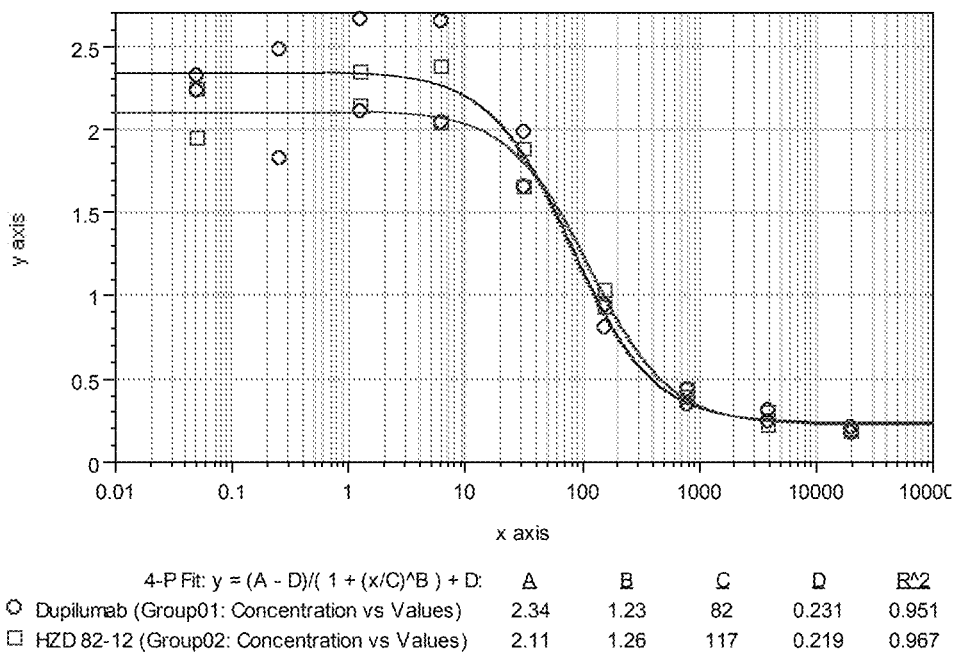

| | 4-P Fit: y = (A - D)/( 1 + (x/C)^B ) + D: | A | B | C | D | R^2 |
|---|---|---|---|---|---|---|
| ○ | Dupilumab (Group01: Concentration vs Values) | 2.34 | 1.23 | 82 | 0.231 | 0.951 |
| □ | HZD 82-12 (Group02: Concentration vs Values) | 2.11 | 1.26 | 117 | 0.219 | 0.967 |

Figure 9(D)

```
                 10        20        30        40        50        60        70
         ----+---------+---------+---------+---------+---------+---------+---------
Human    MKVLQEPTCVSDYMSISTCEWKMNGPTNCSTELRLLYQLVFLLSEAHTCIPENNGGAGCVCHLLMDDVVS
Marmoset MKVLQEPTCVSDYISLSTCEWKMGGPTNCSAELRLVYQLVFLISETNMCVPENNGAAGCVCHLFMEDMVG
                        *        *     *  *  *  *** *       *          * * * *

80        90       100       110       120       130       140
         ----+---------+---------+---------+---------+---------+---------+---------
Human    ADNYTLDLWAGQQLLWKGSFKPSEHVKPRAPGNLTVHTNVSDTLLLTWSNPYPPDNYLYNHLTYAVNIWS
Marmoset ADNYTLDLWAGQQLLWKGSFKPSEHVKPKAPENLTVYTNVSETLLLTWSNPYPPDNYLYEKLTYAVNIWN
                                    *   *   *  *                    **        *

150       160       170       180       190       200
         ----+---------+---------+---------+---------+---------+------
Human    ENDPADFRIYNVTYLEPSLRIAASTLKSGISYRARVRAWAQCYNTTWSEWSPSTKWHNSYREPFEQH
Marmoset ENDPTDSRIYDVTYQEPTLRIAASTLKSGVSYRARVRAWAQSYNSTWSEWSPSTKWYNAYKEPFEKH
             * *    *     *  *              *          * *         *** *
```

Figure 10(A)

| Regions | Sequence |
|---|---|

| Regions | Sequence |
|---|---|
| Loop1 | D12YMS15 |
| Loop2 | V40FLLSEA46 |
| Loop3 | M65DDVVSADN73 |

Figure 10(B)

SEQUENCE LISTING

```
<160> NUMBER OF SEQ ID NOS: 23

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence:
      artificially synthesized sequence

<400> SEQUENCE: 1

Thr Asn Ser Met Ser
1               5

<210> SEQ ID NO 2
<211> LENGTH: 16
<212> TYPE: PRT
<213> ORGANISM: Artificial Sequence
<220> FEATURE:
```

```
<223> OTHER INFORMATION: Description of Artificial Sequence:
      artificially synthesized sequence

<400> SEQUENCE: 2

Ile Ile Gly Ser Ser Gly Tyr Met Asp Tyr Ala Ser Trp Ala Lys Gly
1               5                   10                  15

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence:
      artificially synthesized sequence

<400> SEQUENCE: 3

His Gly Asp Ser Ser Ser Phe Ala Leu
1               5

<210> SEQ ID NO 4
<211> LENGTH: 13
<212> TYPE: PRT
<213> ORGANISM: Artificial Sequence
<220> FEATURE:
<223> OTHER INFORMATION: Description of Artificial Sequence:
      artificially synthesized sequence

<400> SEQUENCE: 4

Arg Ala Ser Glu Ser Val Tyr Lys Asn Asn Arg Leu Ser
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence:
      artificially synthesized sequence

<400> SEQUENCE: 5

Glu Ala Ser Lys Val Ala Ser
1               5

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence:
      artificially synthesized sequence

<400> SEQUENCE: 6

Ala Gly Ala Tyr Arg Gly Asn Ile Tyr Pro
1               5                   10

<210> SEQ ID NO 7
<211> LENGTH: 117
<212> TYPE: PRT
<213> ORGANISM: Artificial Sequence
<220> FEATURE:
<223> OTHER INFORMATION: Description of Artificial Sequence:
      artificially synthesized sequence

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Ile Asp Leu Arg Thr Asn
```

```
                    20                  25                  30

Ser Met Ser Trp Val Arg Gln Ala Pro Gly Lys Gly Leu Glu Trp Val
                35                  40                  45

Gly Ile Ile Gly Ser Ser Gly Tyr Met Asp Tyr Ala Ser Trp Ala Lys
        50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg His Gly Asp Ser Ser Ser Phe Ala Leu Trp Gly Gln Gly Thr Leu
            100                 105                 110

Val Thr Val Ser Ser
            115

<210> SEQ ID NO 8
<211> LENGTH: 110
<212> TYPE: PRT
<213> ORGANISM: Artificial Sequence
<220> FEATURE:
<223> OTHER INFORMATION: Description of Artificial Sequence:
      artificially synthesized sequence

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Tyr Lys Asn
                20                  25                  30

Asn Arg Leu Ser Trp Tyr Gln Lys Pro Gly Lys Ala Pro Lys Leu
            35                  40                  45

Leu Ile Tyr Glu Ala Ser Lys Val Ala Ser Gly Val Pro Ser Arg Phe
        50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Ala Gly Ala Tyr Arg Gly
                85                  90                  95

Asn Ile Tyr Pro Phe Gly Gln Gly Thr Lys Val Glu Ile Lys
            100                 105                 110

<210> SEQ ID NO 9
<211> LENGTH: 232
<212> TYPE: PRT
<213> ORGANISM: Artificial Sequence
<220> FEATURE:
<223> OTHER INFORMATION: Description of Artificial Sequence:
      artificially synthesized sequence

<400> SEQUENCE: 9

Met Gly Trp Leu Cys Ser Gly Leu Leu Phe Pro Val Ser Cys Leu Val
1               5                   10                  15

Leu Leu Gln Val Ala Ser Ser Gly Asn Met Lys Val Leu Gln Glu Pro
                20                  25                  30

Thr Cys Val Ser Asp Tyr Met Ser Ile Ser Thr Cys Glu Trp Lys Met
            35                  40                  45

Asn Gly Pro Thr Asn Cys Ser Thr Glu Leu Arg Leu Leu Tyr Gln Leu
        50                  55                  60

Val Phe Leu Leu Ser Glu Ala His Thr Cys Ile Pro Glu Asn Asn Gly
65                  70                  75                  80

Gly Ala Gly Cys Val Cys His Leu Leu Met Asp Asp Val Val Ser Ala
```

```
                    85                  90                  95
Asp Asn Tyr Thr Leu Asp Leu Trp Ala Gly Gln Gln Leu Leu Trp Lys
                100                 105                 110

Gly Ser Phe Lys Pro Ser Glu His Val Lys Pro Arg Ala Pro Gly Asn
            115                 120                 125

Leu Thr Val His Thr Asn Val Ser Asp Thr Leu Leu Leu Thr Trp Ser
        130                 135                 140

Asn Pro Tyr Pro Pro Asp Asn Tyr Leu Tyr Asn His Leu Thr Tyr Ala
145                 150                 155                 160

Val Asn Ile Trp Ser Glu Asn Asp Pro Ala Asp Phe Arg Ile Tyr Asn
                165                 170                 175

Val Thr Tyr Leu Glu Pro Ser Leu Arg Ile Ala Ala Ser Thr Leu Lys
            180                 185                 190

Ser Gly Ile Ser Tyr Arg Ala Arg Val Arg Ala Trp Ala Gln Cys Tyr
        195                 200                 205

Asn Thr Thr Trp Ser Glu Trp Ser Pro Ser Thr Lys Trp His Asn Ser
210                 215                 220

Tyr Arg Glu Pro Phe Glu Gln His
225                 230

<210> SEQ ID NO 10
<211> LENGTH: 444
<212> TYPE: PRT
<213> ORGANISM: Artificial Sequence
<220> FEATURE:
<223> OTHER INFORMATION: Description of Artificial Sequence:
      artificially synthesized sequence

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Ala Ser Gly Ile Asp Leu Arg Thr Asn
            20                  25                  30

Ser Met Ser Trp Val Arg Gln Ala Pro Gly Lys Gly Leu Glu Trp Val
        35                  40                  45

Gly Ile Ile Gly Ser Ser Gly Tyr Met Asp Tyr Ala Ser Trp Ala Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg His Gly Asp Ser Ser Ser Phe Ala Leu Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205
```

-continued

Thr Lys Val Asp Lys Arg Val Glu Ser Lys Tyr Gly Pro Pro Cys Pro
210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
            245                 250                 255

Thr Cys Val Val Val Asp Val Ser Gln Glu Asp Pro Glu Val Gln Phe
        260                 265                 270

Asn Trp Tyr Val Asp Gly Val Glu Val His Asn Ala Lys Thr Lys Pro
            275                 280                 285

Arg Glu Glu Gln Phe Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
            435                 440

<210> SEQ ID NO 11
<211> LENGTH: 217
<212> TYPE: PRT
<213> ORGANISM: Artificial Sequence
<220> FEATURE:
<223> OTHER INFORMATION: Description of Artificial Sequence:
      artificially synthesized sequence

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Tyr Lys Asn
            20                  25                  30

Asn Arg Leu Ser Trp Tyr Gln Gln Lys Pro Gly Lys Ala Pro Lys Leu
        35                  40                  45

Leu Ile Tyr Glu Ala Ser Lys Val Ala Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Ala Gly Ala Tyr Arg Gly
            85                  90                  95

Asn Ile Tyr Pro Phe Gly Gln Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Cys Leu Leu Asn Phe Tyr Pro
        130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 12
<211> LENGTH: 116
<212> TYPE: PRT
<213> ORGANISM: Artificial Sequence
<220> FEATURE:
<223> OTHER INFORMATION: Description of Artificial Sequence:
      artificially synthesized sequence

<400> SEQUENCE: 12

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Asn Ser Asn
            20                  25                  30

Ala Val Gly Trp Val Arg Gln Ala Pro Gly Lys Gly Leu Glu Tyr Ile
        35                  40                  45

Gly Phe Ile Asn Phe Ser Gly Ile Thr Tyr Tyr Ala Asn Trp Ala Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Ser Ala Gly Ser Phe Asp Leu Trp Gly Gln Gly Thr Leu Val
            100                 105                 110

Thr Val Ser Ser
        115

<210> SEQ ID NO 13
<211> LENGTH: 110
<212> TYPE: PRT
<213> ORGANISM: Artificial Sequence
<220> FEATURE:
<223> OTHER INFORMATION: Description of Artificial Sequence:
      artificially synthesized sequence

<400> SEQUENCE: 13

Asp Ile Gln Met Thr Gln Ser Pro Ser Ser Leu Ser Ala Ser Val Gly
1               5                   10                  15

Asp Arg Val Thr Ile Thr Cys Gln Ala Ser Glu Ser Val Tyr Lys Asn
            20                  25                  30

Asn Tyr Leu Ala Trp Tyr Gln Gln Lys Pro Gly Lys Ala Pro Lys Leu
        35                  40                  45

Leu Ile Tyr Arg Ala Ser Asn Leu Ala Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

```
Gln Pro Glu Asp Phe Ala Thr Tyr Tyr Cys Gln Gly Gly Tyr Ser Ser
                85                  90                  95

Gly Met Tyr Pro Phe Gly Gln Gly Thr Lys Val Glu Ile Lys
            100                 105                 110

<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence:
      artificially synthesized sequence

<400> SEQUENCE: 14

Ser Asn Ala Val Gly
1               5

<210> SEQ ID NO 15
<211> LENGTH: 16
<212> TYPE: PRT
<213> ORGANISM: Artificial Sequence
<220> FEATURE:
<223> OTHER INFORMATION: Description of Artificial Sequence:
      artificially synthesized sequence

<400> SEQUENCE: 15

Phe Ile Asn Phe Ser Gly Ile Thr Tyr Tyr Ala Asn Trp Ala Lys Gly
1               5                   10                  15

<210> SEQ ID NO 16
<211> LENGTH: 8
<212> TYPE: PRT
<213> ORGANISM: Artificial Sequence
<220> FEATURE:
<223> OTHER INFORMATION: Description of Artificial Sequence:
      artificially synthesized sequence

<400> SEQUENCE: 16

Gly Ser Ala Gly Ser Phe Asp Leu
1               5

<210> SEQ ID NO 17
<211> LENGTH: 13
<212> TYPE: PRT
<213> ORGANISM: Artificial Sequence
<220> FEATURE:
<223> OTHER INFORMATION: Description of Artificial Sequence:
      artificially synthesized sequence

<400> SEQUENCE: 17

Gln Ala Ser Glu Ser Val Tyr Lys Asn Asn Tyr Leu Ala
1               5                   10

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence:
      artificially synthesized sequence

<400> SEQUENCE: 18

Arg Ala Ser Asn Leu Ala Ser
1               5

<210> SEQ ID NO 19
```

```
<211> LENGTH: 10
<212> TYPE: PRT
<213> ORGANISM: Artificial Sequence
<220> FEATURE:
<223> OTHER INFORMATION: Description of Artificial Sequence:
      artificially synthesized sequence

<400> SEQUENCE: 19

Gln Gly Gly Tyr Ser Ser Gly Met Tyr Pro
1               5                   10

<210> SEQ ID NO 20
<211> LENGTH: 443
<212> TYPE: PRT
<213> ORGANISM: Artificial Sequence
<220> FEATURE:
<223> OTHER INFORMATION: Description of Artificial Sequence:
      artificially synthesized sequence

<400> SEQUENCE: 20

Glu Val Gln Leu Val Glu Ser Gly Gly Leu Val Gln Pro Gly Gly
1               5                   10                  15

Ser Leu Arg Leu Ser Cys Ala Ala Ser Gly Phe Ser Leu Asn Ser Asn
            20                  25                  30

Ala Val Gly Trp Val Arg Gln Ala Pro Gly Lys Gly Leu Glu Tyr Ile
        35                  40                  45

Gly Phe Ile Asn Phe Ser Gly Ile Thr Tyr Tyr Ala Asn Trp Ala Lys
50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Ser Ala Gly Ser Phe Asp Leu Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Lys Thr Tyr Thr Cys Asn Val Asp His Lys Pro Ser Asn Thr
        195                 200                 205

Lys Val Asp Lys Arg Val Glu Ser Lys Tyr Gly Pro Pro Cys Pro Pro
    210                 215                 220

Cys Pro Ala Pro Glu Phe Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Tyr Arg Val Val Ser Val Leu Thr Val
    290                 295                 300
```

```
Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe
                355                 360                 365

Tyr Pro Ser Asp Ile Ala Val Glu Trp Glu Ser Asn Gly Gln Pro Glu
370                 375                 380

Asn Asn Tyr Lys Thr Thr Pro Pro Val Leu Asp Ser Asp Gly Ser Phe
385                 390                 395                 400

Phe Leu Tyr Ser Arg Leu Thr Val Asp Lys Ser Arg Trp Gln Glu Gly
                405                 410                 415

Asn Val Phe Ser Cys Ser Val Met His Glu Ala Leu His Asn His Tyr
                420                 425                 430

Thr Gln Lys Ser Leu Ser Leu Ser Leu Gly Lys
                435                 440

<210> SEQ ID NO 21
<211> LENGTH: 217
<212> TYPE: PRT
<213> ORGANISM: Artificial Sequence
<220> FEATURE:
<223> OTHER INFORMATION: Description of Artificial Sequence:
      artificially synthesized sequence

<400> SEQUENCE: 21

Asp Ile Gln Met Thr Gln Ser Pro Ser Ser Leu Ser Ala Ser Val Gly
1               5                   10                  15

Asp Arg Val Thr Ile Thr Cys Gln Ala Ser Glu Ser Val Tyr Lys Asn
            20                  25                  30

Asn Tyr Leu Ala Trp Tyr Gln Gln Lys Pro Gly Lys Ala Pro Lys Leu
        35                  40                  45

Leu Ile Tyr Arg Ala Ser Asn Leu Ala Ser Gly Val Pro Ser Arg Phe
50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gly Gly Tyr Ser Ser
                85                  90                  95

Gly Met Tyr Pro Phe Gly Gln Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
```

210 215

<210> SEQ ID NO 22
<211> LENGTH: 207
<212> TYPE: PRT
<213> ORGANISM: Artificial Sequence
<220> FEATURE:
<223> OTHER INFORMATION: Description of Artificial Sequence:
      artificially synthesized sequence

<400> SEQUENCE: 22

Met Lys Val Leu Gln Glu Pro Thr Cys Val Ser Asp Tyr Met Ser Ile
1               5                   10                  15

Ser Thr Cys Glu Trp Lys Met Asn Gly Pro Thr Asn Cys Ser Thr Glu
            20                  25                  30

Leu Arg Leu Leu Tyr Gln Leu Val Phe Leu Leu Ser Glu Ala His Thr
        35                  40                  45

Cys Ile Pro Glu Asn Asn Gly Gly Ala Gly Cys Val Cys His Leu Leu
    50                  55                  60

Met Asp Asp Val Val Ser Ala Asp Asn Tyr Thr Leu Asp Leu Trp Ala
65                  70                  75                  80

Gly Gln Gln Leu Leu Trp Lys Gly Ser Phe Lys Pro Ser Glu His Val
                85                  90                  95

Lys Pro Arg Ala Pro Gly Asn Leu Thr Val His Thr Asn Val Ser Asp
            100                 105                 110

Thr Leu Leu Leu Thr Trp Ser Asn Pro Tyr Pro Pro Asp Asn Tyr Leu
        115                 120                 125

Tyr Asn His Leu Thr Tyr Ala Val Asn Ile Trp Ser Glu Asn Asp Pro
    130                 135                 140

Ala Asp Phe Arg Ile Tyr Asn Val Thr Tyr Leu Glu Pro Ser Leu Arg
145                 150                 155                 160

Ile Ala Ala Ser Thr Leu Lys Ser Gly Ile Ser Tyr Arg Ala Arg Val
                165                 170                 175

Arg Ala Trp Ala Gln Cys Tyr Asn Thr Thr Trp Ser Glu Trp Ser Pro
            180                 185                 190

Ser Thr Lys Trp His Asn Ser Tyr Arg Glu Pro Phe Glu Gln His
        195                 200                 205

<210> SEQ ID NO 23
<211> LENGTH: 207
<212> TYPE: PRT
<213> ORGANISM: Artificial Sequence
<220> FEATURE:
<223> OTHER INFORMATION: Description of Artificial Sequence:
      artificially synthesized sequence

<400> SEQUENCE: 23

Met Lys Val Leu Gln Glu Pro Thr Cys Val Ser Asp Tyr Ile Ser Leu
1               5                   10                  15

Ser Thr Cys Glu Trp Lys Met Gly Gly Pro Thr Asn Cys Ser Ala Glu
            20                  25                  30

Leu Arg Leu Val Tyr Gln Leu Val Phe Leu Ile Ser Glu Thr Asn Met
        35                  40                  45

Cys Val Pro Glu Asn Asn Gly Ala Ala Gly Cys Val Cys His Leu Phe
    50                  55                  60

Met Glu Asp Met Val Gly Ala Asp Asn Tyr Thr Leu Asp Leu Trp Ala
65                  70                  75                  80

Gly Gln Gln Leu Leu Trp Lys Gly Ser Phe Lys Pro Ser Glu His Val

-continued

```
                85                  90                  95
Lys Pro Lys Ala Pro Glu Asn Leu Thr Val Tyr Thr Asn Val Ser Glu
            100                 105                 110

Thr Leu Leu Leu Thr Trp Ser Asn Pro Tyr Pro Pro Asp Asn Tyr Leu
            115                 120                 125

Tyr Glu Lys Leu Thr Tyr Ala Val Asn Ile Trp Asn Glu Asn Asp Pro
            130                 135                 140

Thr Asp Ser Arg Ile Tyr Asp Val Thr Tyr Gln Glu Pro Thr Leu Arg
145                 150                 155                 160

Ile Ala Ala Ser Thr Leu Lys Ser Gly Val Ser Tyr Arg Ala Arg Val
                165                 170                 175

Arg Ala Trp Ala Gln Ser Tyr Asn Ser Thr Trp Ser Glu Trp Ser Pro
            180                 185                 190

Ser Thr Lys Trp Tyr Asn Ala Tyr Lys Glu Pro Phe Glu Lys His
            195                 200                 205
```

MONOCLONAL ANTIBODIES AGAINST HUMAN INTERLEUKIN-4 RECEPTOR ALPHA, ENCODING NUCLEIC ACIDS THEREOF AND METHOD OF USE THEREOF TO TREAT IL-4 OR IL-4/IL-13-MEDIATED DISEASES

SEQUENCE LISTING

A sequence listing in electronic (.txt file) format is filed with this application and incorporated herein by reference. The name of the .txt file is "Sequence listing 1013.txt"; the file was created on Sep. 4, 2024; the size of the file is 25,932 bytes.

TECHNICAL FIELD

The present invention relates to the field of antibody drugs. Specifically, the present invention relates to antibodies and fragments thereof, including monoclonal antibody against human interleukin-4 receptor alpha (hIL-4Rα) and use thereof.

BACKGROUND ART

The human interleukin-4 receptor alpha (human IL-4Rα, or hIL-4Rα) subunit is a 140 kDa type I transmembrane protein binding to IL-4 with high affinity. After binding to hIL-4Rα, IL-4 recruits a common gamma chain (the common receptor subunit of IL-2 and many other cytokines) to constitute type I IL-4 receptor, or recruits IL-13Rα1 to constitute type II IL-4 receptor (this receptor can bind to IL-13 to mediate its biological effects), thereby transducing the signal. IL-4Rα can thus mediate the biological activities of IL-4 and IL-13. The type I receptor predominates in hematopoietic cells, and the type II receptor is expressed on both hematopoietic and non-hematopoietic cells. In vitro studies have shown that IL-4 and IL-13 activate the effector functions of a variety of cells (such as T cells, B cells, eosinophils, mast cells, basophils, airway smooth muscle cells, respiratory tract epithelial cells, lung fibroblasts, and endothelial cells) through the type I/II receptors. IL-4 is a key cytokine that promotes the differentiation and development of naive Th cells (helper T cells) into Th2. It can promote the expression of CD23 and MEW II (a major histocompatibility complex) by B cells, the cell activation and the IgE secretion, and can promote the up-regulation of IgE receptor expression by B cells, mast cells, etc., and enhance their reactivity. At the same time, it can promote the release of vascular cell adhesion molecule 1 (VCAM-1) from vascular endothelial cells and then induce the transfer of T cells, monocytes and eosinophils/basophils to the inflammatory sites.

IL-4 and IL-4 receptor complexes, along with modulators of IL-4 receptor activity, are described in Paul, Cytokine 75(1):3-7, 2015; Oh et al., Eur. Respir. Rev. 19(115):48-54, 2010; and Junttila, Frontiers in Immunology 9:888, 2018.

Patent publications indicated to describe IL-4 receptor inhibitors and diseases targeted by IL-4 receptor inhibitors include: U.S. Pat. Nos. 5,714,146, 7,872,113, 8,679,487, 8,877,189, and 8,980,273; U.S. patent publication 2019/0177408; European patent publication EP2791169; and international patent publications WO9414975; WO200162287; WO2005047331; WO2007085815; WO2008054606; WO2008076784; WO2009081201; WO2009114828; WO2009121847; WO2009124090; WO2010070346; WO2014031610; WO2014165771; WO2014197470; WO2014205365; WO2015006571; WO2015127229; WO2015130975; WO2016077675; WO2017211319; WO2018045130; WO2018057776; WO2018102597; and WO2019028367.

SUMMARY OF THE INVENTION

IL-4 plays an important role in the occurrence and development of diseases associated with IL-4- and/or IL-13-mediated signal transduction, such as atopic dermatitis, arthritis (including septic arthritis), herpes, chronic primary urticaria, scleroderma, hypertrophic scar, Whipple's disease, benign prostatic hyperplasia, lung diseases such as mild, moderate and severe asthma, allergic rhinitis, chronic sinusitis, hay fever, chronic obstructive pulmonary disease, and pulmonary fibrosis, eosinophilia, psoriasis, psoriatic arthritis, and inflammatory diseases such as inflammatory bowel disease, allergic reactions, Kawasaki disease, sickle cell disease, Churg-Strauss syndrome, Graves' disease, pre-eruptive purpura, Sjogren's syndrome, autoimmune lymphoproliferative syndrome, autoimmune hemolytic anemia, Barrett's esophagus, autoimmune uveitis, tuberculosis, hereditary allergic dermatitis, ulcerative colitis, fibrosis, and kidney diseases. Similar to IL-4, IL-13 is closely related to the pathological process of allergic diseases, and promotes the hyperplasia of goblet cells, conversion of the type of antibody released by B cells to IgE, induction of chemokine release and then chemotaxis of eosinophils, etc. It can also result in fibrosis of epithelial cells and high reactivity of the respiratory tract.

Dupilumab (trade name Dupixent®), a monoclonal antibody drug targeting hIL-4Rα developed by corporations such as Sanofi, has been approved by the US FDA for the treatment of atopic dermatitis.

In a first aspect, objectives of the present application include providing a novel monoclonal antibody against human interleukin-4 receptor alpha (hIL-4Rα), a pharmaceutical composition comprising the monoclonal antibody, and pharmaceutical use of the monoclonal antibody.

A second aspect of the present invention is directed to an antibody or fragment thereof against hIL-4Rα having heavy chain complementary determining regions as set forth in SEQ ID NOs: 1-3 or 14-16 and light chain complementary determining regions as set forth in SEQ ID NOs: 4-6 or 17-19. Different embodiments include nucleic acid encoding the antibody or fragment thereof, methods of making the antibody or fragment thereof, methods of treatment employing the antibody or fragment thereof, a pharmaceutical composition comprising the antibody or fragment thereof, a pharmaceutical use of the antibody or fragment thereof; and preparation of a medicament containing the antibody or fragment thereof.

That is, the present application includes the following items:

1. An antibody or fragment thereof capable of binding the human IL-4Rα (hIL-4Rα), wherein the antibody or fragment thereof capable of significantly binding the Loop 2 of the human IL-4Rα (hIL-4Rα), especially capable of significantly binding the L42, L43, S44, and E45 in Loop 2 of the hIL-4Rα.

2. The antibody or fragment thereof of item 1, wherein the antibody or fragment thereof no significant binding to the Loop 3 of the human IL-4Rα (hIL-4Rα), especially no significant binding to the M65, D66, D67, V68, V69, S70, A71, D72 and N73 in Loop 3 of the hIL-4Rα.

3. The antibody or fragment thereof of items 1 or 2, wherein the antibody or fragment thereof binds to marmoset IL-4Rα at 90% or greater the level it binds to human IL-4Rα.

4. An antibody or fragment thereof that is either:
  a) a recombinant antibody or fragment thereof against human IL-R4a comprising three heavy chain complementarily region (CDR-H1, CDR-H2 and CDR-H3) and three light chain complementary determining regions (CDR-L1, CDR-L2 and CDR-L3), wherein the amino acid sequence of CDR-H1 is set forth in SEQ ID NO: 1, the amino acid sequence of CDR-H2 is set forth in SEQ ID NO: 2, the amino acid sequence of CDR-H3 is set forth in SEQ ID NO: 3, the amino acid sequence of CDR-L1 is set forth in SEQ ID NO: 4, the amino acid sequence of CDR-L2 is set forth in SEQ ID NO: 5, and the amino acid sequence of CDR-L3 is set forth in SEQ ID NO: 6, or
  b) an isolated monoclonal antibody against human IL-R4α receptor comprising three heavy chain complementarily region (CDR-H1, CDR-H2 and CDR-H3) and three light chain complementary determining regions (CDR-L1, CDR-L2 and CDR-L3), wherein the amino acid sequence of CDR-H1 is set forth in SEQ ID NO: 1, the amino acid sequence of CDR-H2 is set forth in SEQ ID NO: 2, the amino acid sequence of CDR-H3 is set forth in SEQ ID NO: 3, the amino acid sequence of CDR-L1 is set forth in SEQ ID NO: 4, the amino acid sequence of CDR-L2 is set forth in SEQ ID NO: 5, and the amino acid sequence of CDR-L3 is set forth in SEQ ID NO: 6.

5. The antibody or fragment thereof of item 4, wherein said antibody or fragment thereof is said isolated monoclonal antibody.

6. The antibody or fragment thereof of item 5, wherein said isolated monoclonal antibody comprises a heavy chain variable region and a light chain variable region, wherein the amino acid sequence of the heavy chain variable region is set forth in SEQ ID NO: 7 and the amino acid sequence of the light chain variable region is set forth in SEQ ID NO: 8.

7. The antibody or fragment thereof of item 4, wherein said antibody or fragment thereof is said recombinant antibody or fragment thereof.

8. The antibody or fragment thereof of item 7, wherein said recombinant antibody or fragment thereof is humanized.

9. The antibody or fragment thereof of item 8, wherein said recombinant antibody or fragment thereof comprises a heavy chain variable region comprising the amino acid sequence set forth in SEQ ID NO: 7 and a light chain variable region comprising the sequence set forth in SEQ ID NO: 8.

10. The antibody or fragment thereof of item 9, wherein said recombinant antibody or fragment thereof is an IgG4 antibody.

11. The antibody or fragment thereof of item 9, wherein said recombinant antibody or fragment thereof is an antibody comprising the heavy chain amino acid sequence set forth in SEQ ID NO: 10 and the light chain amino acid is set forth in SEQ ID NO: 11.

12. The antibody or fragment thereof of item 11, wherein said antibody is a monoclonal antibody.

13. An antibody or fragment thereof that is either
  a) a recombinant antibody or fragment thereof against human IL-R4α receptor comprising three heavy chain complementarity region (CDR-H1, CDR-H2 and CDR-H3) and three light chain complementary determining regions (CDR-L1, CDR-L2 and CDR-L3), wherein the amino acid sequence of CDR-H1 is set forth in SEQ ID NO: 14, the amino acid sequence of CDR-H2 is set forth in SEQ ID NO: 15, the amino acid sequence of CDR-H3 is set forth in SEQ ID NO: 16, the amino acid sequence of CDR-L1 is set forth in SEQ ID NO: 17, the amino acid sequence of CDR-L2 is set forth in SEQ ID NO: 18, and the amino acid sequence of CDR-L3 is set forth in SEQ ID NO: 19; or
  b) an isolated monoclonal antibody against human IL-R4α receptor comprising three heavy chain complementarity region (CDR-H1, CDR-H2 and CDR-H3) and three light chain complementary determining regions (CDR-L1, CDR-L2 and CDR-L3),
  wherein the amino acid sequence of CDR-H1 is set forth in SEQ ID NO: 14, the amino acid sequence of CDR-H2 is set forth in SEQ ID NO: 15, the amino acid sequence of CDR-H3 is set forth in SEQ ID NO: 16, the amino acid sequence of CDR-L1 is set forth in SEQ ID NO: 17, the amino acid sequence of CDR-L2 is set forth in SEQ ID NO: 18, and the amino acid sequence of CDR-L3 is set forth in SEQ ID NO: 19.

14. The antibody or fragment thereof of item 13, wherein said antibody or fragment thereof is said isolated monoclonal antibody.

15. The antibody or fragment thereof of item 14, wherein said isolated monoclonal antibody comprises a heavy chain variable region and a light chain variable region, wherein the amino acid sequence of the heavy chain variable region is set forth in SEQ ID NO: 12 and the amino acid sequence of the light chain variable region is set forth in SEQ ID NO: 13.

16. The antibody or fragment thereof of item 13, wherein said antibody or fragment thereof is said recombinant antibody or fragment thereof.

17. The antibody or fragment thereof of item 16, wherein said recombinant antibody or fragment thereof is humanized.

18. The antibody or fragment thereof of item 17, wherein said recombinant antibody or fragment thereof comprises a heavy chain variable region comprising the amino acid sequence set forth in SEQ ID NO: 12 and a light chain variable region comprising the sequence set forth in SEQ ID NO: 13.

19. The antibody or fragment thereof of item 18, wherein said recombinant antibody or fragment thereof is an IgG4 antibody.

20. The antibody or fragment thereof of item 17, wherein said recombinant antibody or fragment thereof is an antibody comprising the heavy chain amino acid sequence set forth in SEQ ID NO: 20 and the light chain amino acid sequence set forth in SEQ ID NO: 21.

21. The antibody or fragment thereof of item 20, wherein said antibody is a monoclonal antibody.

22. An isolated nucleic acid encoding the antibody or fragment thereof of anyone of items 1-11 and 13-20.

23. A host cell comprising the isolated nucleic acid of item 22.

The nucleic acid can be present on a vector. The vector may be of any type, for example, a recombinant vector such as an expression vector. Any of a variety of host cells can be used. In one embodiment, the host cell is a prokaryotic cell, e.g., *E. coli*. In another embodiment, the host cell is a eukaryotic cell, e.g., a mammalian cell, such as Chinese hamster ovary (CHO) cell.

24. A method of producing a monoclonal antibody comprising the step of expressing a nucleic acid encoding the monoclonal antibody of anyone of items 5, 6, 14 or 15 in a host cell.

25. The method of item 24, wherein said host cell is CHO or HEK293.

26. A method of producing the antibody or fragment thereof of any one of items 1-4, 7-13 and 16-21, comprising the step of expressing a nucleic acid encoding said antibody or fragment thereof.

27. The method of item 26, wherein said host cell is CHO or HEK293.

The above methods comprise a recombinant expressing vector encoding the monoclonal antibody or fragment thereof against human interleukin-4 receptor alpha (hIL-4Rα) in a suitable host cell to produce the monoclonal antibody. In certain embodiments, the method comprises culturing a host cell comprising a nucleic acid encoding the monoclonal antibody against human interleukin-4 receptor alpha (hIL-4Rα) to express the nucleic acid. The method may further comprise recovering the monoclonal antibody against human interleukin-4 receptor alpha (hIL-4Rα) from a host cell culture or a host cell culture medium.

28. An antibody or fragment thereof produced by the method of items 24 or 25.

29. An antibody or fragment thereof produced by the method of items 26 or 27.

30. A pharmaceutical composition comprising the antibody or fragment of anyone of items 1-21, 28 and 29 and a pharmaceutically acceptable carrier.

The pharmaceutical composition may further comprise an additional therapeutic agent (e.g., a different antibody against human interleukin-4 receptor alpha (hIL-4Rα)).

31. A method of treating a disease mediated IL-4 or IL-4/IL-13 signal transduction comprising the step of administering to a human patient in need thereof an effective amount of the antibody or fragment thereof of anyone of items 1-21, 28 and 29.

32. The method of item 31, wherein said disease is selected from the group consisting of: atopic dermatitis, hereditary allergic dermatitis, arthritis (including septic arthritis), herpes, chronic primary urticaria, scleroderma, hypertrophic scar, Whipple's disease, benign prostatic hyperplasia, lung diseases such as mild, moderate and severe asthma, allergic rhinitis, chronic sinusitis, hay fever, chronic obstructive pulmonary disease, and pulmonary fibrosis, eosinophilia, psoriasis, psoriatic arthritis, and inflammatory diseases such as ulcerative colitis, inflammatory bowel disease, allergic reactions, Kawasaki disease, sickle cell disease, Churg-Strauss syndrome, Graves' disease, pre-eruptive purpura, Sjogren's syndrome, autoimmune lymphoproliferative syndrome, autoimmune hemolytic anemia, Barrett's esophagus, autoimmune uveitis, tuberculosis, fibrosis, and kidney diseases.

33. The method of item 31, wherein said disease is selected from the group consisting of: asthma, atopic dermatitis, eczema, sinusitis, nasal polyposis, nasal polyps, sclerosis, eosinophilic oesophagitis, allergic oesophagitis, oesophagitis, Sjogren's syndrome, chronic obstructive pulmonary disease and emphysema.

34. The method of item 32, wherein said disease is atopic dermatitis.

35. The method of item 32, wherein said disease is asthma.

36. A pharmaceutical composition according to item 30, for use in the treatment of a disease mediated IL-4 or IL-4/IL-13 signal transduction.

37. The pharmaceutical composition of item 36, wherein said disease is selected from the group consisting of atopic dermatitis, hereditary allergic dermatitis, arthritis (including septic arthritis), herpes, chronic primary urticaria, scleroderma, hypertrophic scar, Whipple's disease, benign prostatic hyperplasia, lung diseases such as mild, moderate and severe asthma, allergic rhinitis, chronic sinusitis, hay fever, chronic obstructive pulmonary disease, and pulmonary fibrosis, eosinophilia, psoriasis, psoriatic arthritis, and inflammatory diseases such as ulcerative colitis, inflammatory bowel disease, allergic reactions, Kawasaki disease, sickle cell disease, Churg-Strauss syndrome, Graves' disease, pre-eruptive purpura, Sjogren's syndrome, autoimmune lymphoproliferative syndrome, autoimmune hemolytic anemia, Barrett's esophagus, autoimmune uveitis, tuberculosis, fibrosis, and kidney diseases.

38. The pharmaceutical composition of item 36, wherein said disease is selected from the group consisting of: asthma, atopic dermatitis, eczema, sinusitis, nasal polyposis, nasal polyps, sclerosis, eosinophilic oesophagitis, allergic oesophagitis, oesophagitis, Sjogren's syndrome, chronic obstructive pulmonary disease and emphysema.

39. Use of antibody or fragment thereof according to anyone of items 1-21, 28 and 29 in the preparation of a medicament for the treatment of a disease associated with IL-4 and/or IL-13-mediated signal transduction.

40. The use of item 39, wherein said disease is selected from the group consisting of atopic dermatitis, hereditary allergic dermatitis, arthritis (including septic arthritis), herpes, chronic primary urticaria, scleroderma, hypertrophic scar, Whipple's disease, benign prostatic hyperplasia, lung diseases such as mild, moderate and severe asthma, allergic rhinitis, chronic sinusitis, hay fever, chronic obstructive pulmonary disease, and pulmonary fibrosis, eosinophilia, psoriasis, psoriatic arthritis, and inflammatory diseases such as ulcerative colitis, inflammatory bowel disease, allergic reactions, Kawasaki disease, sickle cell disease, Churg-Strauss syndrome, Graves' disease, pre-eruptive purpura, Sjogren's syndrome, autoimmune lymphoproliferative syndrome, autoimmune hemolytic anemia, Barrett's esophagus, autoimmune uveitis, tuberculosis, fibrosis, and kidney diseases.

41. The use of item 39, wherein said disease is selected from the group consisting of: asthma, atopic dermatitis, eczema, sinusitis, nasal polyposis, nasal polyps, sclerosis, eosinophilic oesophagitis, allergic oesophagitis, oesophagitis, Sjogren's syndrome, chronic obstructive pulmonary disease and emphysema.

Effects of the Invention

The present invention provides an antibody and fragments thereof, including a novel monoclonal antibody, against human interleukin-4 receptor alpha (hIL-4Rα). As illustrated by the novel monoclonal antibodies in the Examples below the described antibodies and fragments thereof can bind to hIL-4Rα with a high affinity and then inhibit IL-4- and/or IL-13-mediated signal transduction and biological effects. Uses of antibodies and fragments thereof include the ability to effectively inhibit the pathological development of diseases associated with IL-4- and/or IL-13-mediated signal transduction. Therefore, the describe antibodies and fragments thereof have active preventive and therapeutic values.

BRIEF DESCRIPTION OF THE DRAWINGS

FIG. 1(A) is a graph showing the results of nucleic acid electrophoresis of QX005N (PD2-31), wherein M: Marker; lane 1: pHZDCH, HindIII/NheI; lane 2: pUC57-2VH-Hu1, HindIII/NheI; lane 3: pHZDCK, HindIII/BsiWI; and lane 4: PCR product 2VK-pd18, HindIII/BsiWI. FIG. 1(B) is a graph showing the results of nucleic acid electrophoresis of QX005N (HZD82-12), wherein M: Marker; lane 1: pHZDCH, HindIII/NheI; lane 2: PCR product 82VH-Hu3, HindIII/NheI; lane 3: pHZDCK, HindIII/BsiWI; and lane 4: pUC57-82VK-Hu1, HindIII/BsiWI.

FIG. 3(A) is a graph showing the electrophoresis result of QX005N (PD2-31), and FIG. 3(B) is a graph showing the electrophoresis result of QX005N (HZD82-12).

FIG. 4(A) shows the results indicating that PD2-31 inhibits the IL-4-induced STAT6 phosphorylation activity in the HEK Blue™ IL-4/IL-13 cells, FIG. 4(B) shows the results indicating that HZD82-12 inhibits the IL-4-induced STAT6 phosphorylation activity in the HEK Blue™ IL-4/IL-13 cells, FIG. 4(C) shows the results indicating that PD2-31 inhibits the IL-13-induced STAT6 phosphorylation activity in the HEK Blue™ IL-4/IL-13 cells, and FIG. 4(D) shows the results indicating that HZD82-12 inhibits the IL-13-induced STAT6 phosphorylation activity in the HEK Blue™ IL-4/IL-13 cells.

FIG. 5(A) shows the results indicating that PD2-31 inhibits the IL-4-induced CCL-17 release activity in the A549 cells, FIG. 5(B) shows the results indicating that HZD82-12 inhibits the IL-4-induced CCL-17 release activity in the A549 cells, FIG. 5(C) shows the results indicating that PD2-31 inhibits the IL-13-induced CCL-17 release activity in the A549 cells, and FIG. 5(D) shows the results indicating that HZD82-12 inhibits the IL-13-induced CCL-17 release activity in the A549 cells.

FIG. 6(A) shows the results indicating that PD2-31 inhibits the IL-4-induced proliferation activity of the TF-1 cells, FIG. 6(B) shows the results indicating that HZD82-12 inhibits the IL-4-induced proliferation activity of the TF-1 cells, FIG. 6(C) shows the results indicating that PD2-31 inhibits the IL-13-induced proliferation activity of the TF-1 cells, and FIG. 6(D) shows the results indicating that HZD82-12 inhibits the IL-13-induced proliferation activity of the TF-1 cells.

FIG. 7(A) shows the results indicating that PD2-31 inhibits the IL-4-induced CCL-11 release activity in the HFL-1 cells, FIG. 7(B) shows the results indicating that HZD82-12 inhibits the IL-4-induced CCL-11 release activity in the HFL-1 cells, FIG. 7(C) shows the results indicating that PD2-31 inhibits the IL-13-induced CCL-11 release activity in the HFL-1 cells, and FIG. 7(D) shows the results indicating that HZD82-12 inhibits the IL-13-induced CCL-11 release activity in the HFL-1 cells.

FIG. 8(A) shows the results of inhibiting the IL-4-induced CD23 expression activity in the PBMCs, and FIG. 8(B) shows the results of inhibiting the IL-13-induced CD23 expression activity in the PBMCs. Dup in the figures indicates Dupilumab.

FIG. 9(A)-9(D) are graphs showing that QX005N inhibits the IL-4- or IL-13-induced CCL-17 release activity in the PBMCs. FIG. 9(A) shows the results indicating that PD2-31 inhibits the IL-4-induced CCL-17 release activity in the PBMCs, FIG. 9(B) shows the results indicating that HZD82-12 inhibits the IL-4-induced CCL-17 release activity in the PBMCs, FIG. 9(C) shows the results indicating that PD2-31 inhibits the IL-13-induced CCL-17 release activity in the PBMCs, and FIG. 9(D) shows the results indicating that HZD82-12 inhibits the IL-13-induced CCL-17 release activity in the PBMCs.

FIG. 10(A)-10(B) shows the alignment results between Human and Marmoset IL-4Rα, and the loop regions of human IL-4Rα. FIG. 10(A) shows the alignment results between Human (SEQ ID NO: 22) and Marmoset (SEQ ID NO: 23) IL-4Rα. FIG. 10(B) shows the loop regions of human IL-4Rα (SEQ ID NO: 22).

DETAILED DESCRIPTION OF EMBODIMENTS

Figure 1A:
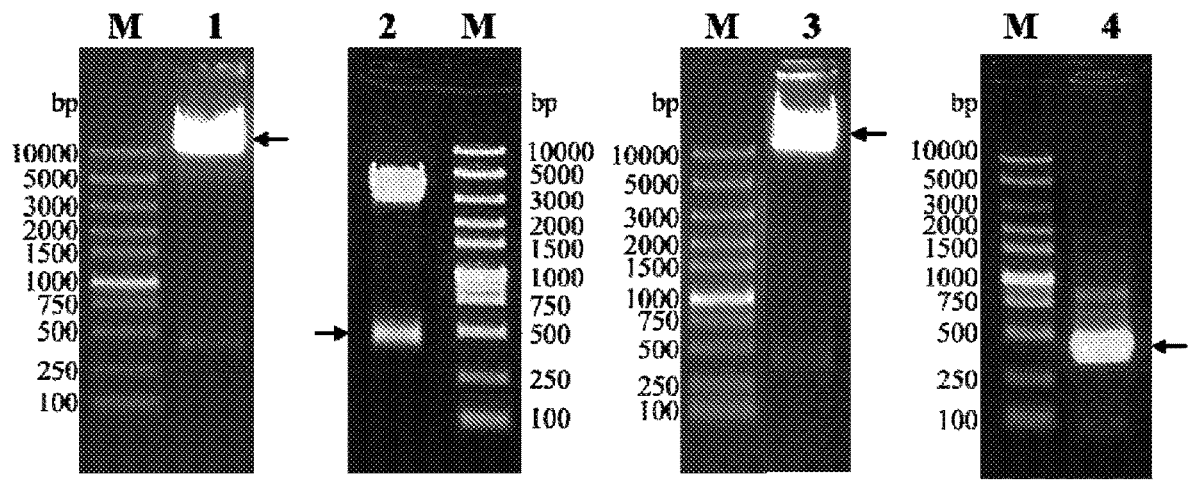
FIG. 1(A)-1(B) are graphs showing the results of nucleic acid electrophoresis of constructing QX005N transient expression plasmids.

The present application provides antibodies and fragments thereof, that bind hIL-4Rα with a high affinity and inhibit IL-4- and/or IL-13-mediated signal transduction and biological effects. Two exemplified antibodies are PD2-31 and HZD82-12. The Examples also include data illustrating one or more advantages of PD2-31 compared to Dupilumab. Dupilumab is a clinically approved monoclonal antibody targeting hIL-4Rα. The provided data point to PD2-31 binding to a different epitope than Dupilumab, PD2-31 having better activity in inhibiting IL-4/IL-13 signal transduction in different assays, and PD2-31 binding to marmoset IL-4Rα. Additionally, PD2-31 binding to a different epitopes than Dupilumab, coupled with Dupilumab having a stronger $K_D$, but lower activity in different assays, suggests that PD2-31 inhibitory activity may have an additional inhibitory component compared to Dupilumab which may also offer further advantages.

The scientific and technical terms mentioned in the specification have the same meanings as those generally understood by persons skilled in the art, and if there is any conflict, the definitions in the specification shall prevail.

In general, the terms used in the specification have the following meanings.

In the specification, an "isolated" antibody is an antibody that has been separated from the components of its natural environment. In certain embodiments, the antibody is purified to a purity of greater than 95% or 99%. The purity is determined by, for example, electrophoresis (e.g., SDS-PAGE isoelectric focusing (IEF), capillary electrophoresis) or chromatography (e.g., ion exchange or reverse phase HPLC). For a review of methods for evaluating antibody purity, see, for example, Flatman et al., J. Chromatogr. B848: 79-87 (2007).

In the specification, a "monoclonal antibody" means an antibody obtained from a substantially homologous antibody population, i.e., the individual antibodies constituting the population are identical and/or bind to the same epitope, with exception of possible variant antibodies (for example, containing naturally occurring mutations or produced during the production of monoclonal antibody formulations) generally present in a minor amount. Each monoclonal antibody in a monoclonal antibody formulation directs against a single determinant on the antigen as compared with a polyclonal antibody formulation that generally includes different antibodies directing against different determinants (epitopes). Thus, the modifier "monoclonal" indicates the character of the antibody as being obtained from a substantially homologous antibody population, and should not be construed as requiring any particular method to produce the antibody. For example, the monoclonal antibody to be used in accordance with the present invention can be prepared by a variety of techniques including, but not limited to, hybridoma methods, recombinant DNA methods, phage display methods, and the methods that use a transgenic animal comprising all or part of the human immunoglobulin gene locus. Such methods and other exemplary methods of preparing the monoclonal antibody are described herein.

In the specification, "affinity" means the strength of the sum of non-covalent interactions between a single binding site of a molecule (e.g., an antibody) and its binding partner (e.g., an antigen). "Binding affinity" as used in the specification, means an intrinsic binding affinity that reflects a 1:1 interaction between members of a binding pair (e.g., an antibody and an antigen), unless otherwise indicated. The affinity of molecule X for its partner Y can generally be expressed by the equilibrium dissociation constant ($K_D$). The affinity can be measured by common methods known in the art.

In the specification, human interleukin-4 receptor alpha (hIL-4Rα, in some cases also simply written as IL-4Rα) means a human-derived protein whose extracellular domain has an amino acid sequence as set forth in SEQ ID. NO: 9, wherein the underlined portion indicates a signal peptide.

```
SEQ ID NO: 9:
MGWLCSGLLFPVSCLVLLQVASSGNMKVLQEPTCVSDYMSISTCEWKMN

GPTNCSTELRLLYQLVFLLSEAHTCIPENNGGAGCVCHLLMDDVVSADN

YTLDLWAGQQLLWKGSFKPSEHVKPRAPGNLTVHTNVSDTLLLTWSNPY

PPDNYLYNHLTYAVNIWSENDPADFRIYNVTYLEPSLRIAASTLKSGIS

YRARVRAWAQCYNTTWSEWSPSTKWHNSYREPFEQH
```

In the specification, "a monoclonal antibody against human interleukin-4 receptor alpha" means a monoclonal antibody that is capable of binding human interleukin-4 receptor alpha with a sufficient affinity such that the monoclonal antibody can be used as a diagnostic and/or therapeutic agent targeting human interleukin-4 receptor alpha.

In some embodiments, an antibody or fragment thereof significantly binding L42, L43, S44, and E45 in Loop 2 of the hIL-4Rα. In the specification, significantly binding one amino acid or several amino acids is indicated by the fold change of the value of equilibrium dissociation constant ($K_D$). If one amino acid is mutated or several amino acids are mutated, and the $K_D$ of antibody binding to such mutated protein is increased 10 times higher than the protein without such amino acid or those amino acids mutations (i.e., the fold change is more than 10), it means the binding activity of antibody is significantly changed by this site mutation or these sites' mutations, and which indicates that the binding activity of antibody is significantly changed, and means the antibody significantly binds these amino acids.

In some embodiments, an antibody or fragment thereof does not significantly bind to Loop 3 of the human IL-4Rα (hIL-4Rα), especially no significant binding to the M65, D66, D67, V68, V69, S70, A71, D72 and N73 in Loop 3 of the hIL-4Rα. In the specification, not significantly binding one amino acid or several amino acids is indicated by the fold change of the value of equilibrium dissociation constant ($K_D$). If one amino acid is mutated or several amino acids are mutated, and the $K_D$ of antibody binding to such mutated protein is less than 10 times of the $K_D$ of the protein without such amino acid or those amino acids mutations (i.e., the fold change is from 1 to less than 10), it means the binding activity of antibody is not reduced by this site mutation or these sites' mutations, and these mutated sites are not the epitope of antibody, and means the antibody does not significantly bind to these amino acids.

In the specification, the above value of equilibrium dissociation constant ($K_D$) is determined by Surface Plasmon Resonance (SPR).

In the specification, the term "epitope" refer to a part of an antigen that can be recognized by antibodies.

As illustrated in the Examples, the biological activities of PD2-31 compare favorably with Dupilumab. The biological activities are, for example, the inhibition of the IL-4- and/or IL-13-induced STAT6 phosphorylation activity in cells, the inhibition of the IL-4- and/or IL-13-induced CCL-17 release activity in A549 cells and PBMCs, the inhibition of the IL-4- and/or IL-13-induced cell proliferation activity, the inhibition of the IL-4- and/or IL-13-induced CCL-11 release activity in cells.

In one embodiment, the heavy chain amino acid sequence of the monoclonal antibody against human interleukin-4 receptor alpha (IL-4Rα) of the present invention is set forth in SEQ ID NO: 10; and the light chain amino acid sequence is set forth in SEQ ID NO: 11.

In another embodiment, the heavy chain amino acid sequence of the monoclonal antibody against human interleukin-4 receptor alpha (IL-4Rα) of the present invention is set forth in SEQ ID NO: 20; and the light chain amino acid sequence is set forth in SEQ ID NO: 21.

SEQ ID NOs: 10 and 11, as well as 20 and 21 are all humanized sequences.

In the specification, an "isolated" nucleic acid means a nucleic acid molecule that has been separated from the components of its natural environment. An isolated nucleic acid includes a nucleic acid molecule comprised in a cell that generally contains the nucleic acid molecule, but the nucleic acid molecule is present extrachromosomally or at a chromosomal location different from its natural chromosomal location.

In the specification, "an isolated nucleic acid encoding a monoclonal antibody against human interleukin-4 receptor alpha" means one or more nucleic acid molecules encoding the heavy and light chains of the antibody, including such nucleic acid molecules in a single vector or separate vectors, as well as such nucleic acid molecules present at one or more positions in a host cell.

In the specification, a "vector" means a nucleic acid molecule capable of amplifying another nucleic acid to which it is linked. The term encompasses a vector that is a self-replicating nucleic acid structure and a vector that is integrated into the genome of the host cell into which it has been introduced. Certain vectors are capable of directing the expression of nucleic acids to which they are operably linked. Such vectors are herein referred to as "expression vectors".

In the specification, "host cell", "host cell line" and "host cell culture" are used interchangeably and means a cell in which an exogenous nucleic acid has been introduced, including the progeny of such a cell. Host cells encompass "transformants" and "transformed cells" which include primary transformed cells and the progenies derived therefrom (regardless of the number of passages). The progenies may not be entirely identical to the parent cell in terms of the nucleic acid content, but may contain mutations. Mutant progenies having the same function or biological activity that are screened or selected for the originally transformed cells are included in the specification.

In the specification, a "pharmaceutical composition" means an article of manufacture which is in such a form that the biological activity of active ingredients contained therein is effective, and which does not contain additional components that are unacceptably toxic to the subject to be administered the formulation.

In the specification, a "pharmaceutically acceptable carrier" means a component other than the active ingredients in the pharmaceutical composition, which is not toxic to the subject. Pharmaceutically acceptable carriers include, but are not limited to, buffers, excipients, stabilizers or preservatives.

Reference to "patient" indicates a human being treated.

Antibody and Antibody Fragments

Antibody (which includes monoclonal antibody) and antibody fragments binding hIL-4Rα (also referred to herein as IL-4Rα binding agents), comprise an antibody heavy chain variable region able to bind hIL-4Rα. Preferably, the IL-4Rα binding agent also comprises a variable light chain region combines with the heavy chain to provide for binding specificity to hIL-4Rα.

An antibody comprises two identical polypeptide heavy chains and two polypeptide light chains. The polypeptides are joined together by noncovalent bonds and disulfide bridges forming a Y shape configuration. Two Fab fragments formed by a light chain ($V_L$—$C_L$) and a heavy chain region ($V_H$—$C_{H1}$), provide for the top of the Y. Each variable region has three hypervariable or complementarity determining regions (CDR-1, CDR-2, and CDR-3) interspaced within a framework region. The CDR's provide specificity determining residues (SDR's) that contact an epitope. In some cases, framework residues can also be helpful or important for epitope binding. Each heavy chain $C_{H1}$ region is covalently joined to additional heavy chain constant regions through a hinge region, where the two heavy chain constant regions are linked together forming an Fc region, which can be visualized as the stem of the antibody Y configuration. The heavy chains are optionally glycosylated.

The IL-4Rα binding agent variable region is preferably humanized. Human variable regions are important for reducing the possibility of a human patient immune system attacking the binding agent. A humanized variable region has one or more non-human CDR's in a framework having an increased number of solvent exposed human amino acid residues, compared to a non-human framework from which the non-human CDR's were obtained. Two general techniques for humanizing are: (1) CDR grafting; and (2) framework resurfacing. CDR grafting involves inserting CDR regions into a human framework region, which may be further modified, for example by back mutations important or helpful for antigen binding. Framework resurfacing involves modifying surface exposed residues of a non-human framework to provide for a human exposed region less likely to induce an immune response in a human. (Frontiers in Bioscience, 13:1619-1633, 2008; and Chiu and Gilliland, Current Opinion in Structural Biology, 38:163-173, 2016.)

The CDR's illustrated in the Examples below were obtained starting from rabbit antibodies. Grafting all six CDR's into a human framework followed by fine tuning the framework is a frequently employed technique for humanizing mouse and rabbit antibodies. (Weber et al., Experimental & Molecular Medicine 49:E305.) Zhang and Ho, MABS, 9:419-429 2017, illustrate humanization of rabbit antibodies involving identification and grafting of combined Kabat/IMGT/Paratome CDR's into a human germline framework followed by additional framework mutations to optimize the antibody.

The antibody Fc region provides for different effectors functions and defines the antibody class and subclass. Human antibody classes are IgM, IgG, IgA, IgD and IgE. IgG can be split into subclasses IgG1, IgG2, IgG3, and IgG4. IgA can be split into subclasses IgA1 and IgA2. The Fc region can mediate effector function through binding to effector cell Fc receptors and by activating other immune mediators. Fc glycosylation plays a part in impacting Fc effector functions. (Schroeder et al., J. Allergy Clin. Imunol, 125(202):541-552, 2010.)

IgG Fc effector functions vary depending on the IgG subclass and may include antibody dependent cell-mediated cytotoxicity, antibody dependent cellular phagocytosis, complement activity, and increased half-life. IgG Fc regions can be modified to increase or decrease effector functions. (Wang et al., Protein Cell 9(1):63-73, 2018; and Strohl, Protein Cell 9(1)86-120, 2018). In an embodiment, the IL-4Rα binding agent is an IgG antibody.

Reference to "IgG" includes different IgG classes and subclasses having a naturally occurring sequence; or a modified sequence where one or more residues are altered, preferably, to increase stability and/or altered to modify effector function (e.g., to reduce cell killing and/or enhance antibody half-life). In an embodiment, the IgG heavy chain has 1, 2, 3, 4, 5, 6, 7, 8, 9 or 10 amino acid differences from a naturally occurring sequence and/or heavy chain constant sequence provided herein. Each amino acid difference is an addition, a substitution, or a deletion. In a further embodiment, the IgG is the IgG4 subtype. IgG4 has a limited ability to induce effector functions leading to cell killing. IgG4 can be modified, for example to alter effector function or reduce Fab-arm exchange. (Davies and Sutton Immunological Reviews 268; 139-159, 2015.)

Antibody fragments binding to IL-4Rα include a Fab fragment, single chain Fv (scFv), domain antibody, minibody, diabody, triabody, and bispecific constructs. Bispecific constructs contain at least two different variable regions providing for specificity to different epitopes. Reference to antibody indicates a full-length antibody; while reference to a fragment thereof indicates a construct comprising at least one of the variable regions as provided in the reference antibody, which could include a bispecific construct. The bispecific may target two different IL-4Rα epitopes, or may target an IL-4Rα epitope along with an epitope on a different entity such as IL-13R. A variety of bispecific constructs are possible including full-length antibody constructs with different variable regions, less than full-length antibodies with different variable regions, and full-length antibodies having appended variable regions. (Strohl, Protein Cell 9(1)86-120, 2018.)

Antibody and antibody fragment half-life can be increased, which can be useful in reducing dosage and dosing frequency. As noted above, the Fc region can be modified to increase antibody half-life. Additional techniques for increasing half-life include addition of a PEG group, fusion to another protein, and delivery strategies such as the use of hydrogels, liposomes, micro/nanoparticles and micelles. (Awwad and Angkawinitwong, Pharmaceutics 10, 83, 2018)

Antibody Production

IL-4Rα binding agents can readily be produced using recombinant cell technology. Potential hosts for recombinant expression include prokaryotic and eukaryotic hosts. The preferred host can be selected taking into account the particular expression product. Prokaryotic hosts may be employed for smaller antibody fragments and where glycosylation is not needed. Eukaryotic host cells, particularly mammalian, are preferred for full-length antibody expression. Mammalian cells lines can be used to produces antibodies with the same folding and post-translation modifications as in humans. Another advantage of mammalian cells lines is the level of secretion. (Frenzel et al., Frontiers in Immunology 4: Article 217, 2013; and Kunert and Reinhart, Appl. Microbiol. Biotechnol. 100:3451-3461, 2016.) In different embodiments, the host cell is either CHO, NSO, Sp2/0, HEK293 or PER.C6; in a further embodiment the host cell is CHO.

IL-4Rα binding agents can be recovered and purified using a variety of different techniques taking into account the particular host cell and the particular antibody and antibody body fragment. Multiple purification steps can be employed. Some examples of recovery and purification steps include affinity chromatography (e.g., Protein A for full length antibodies having an Fc region, Protein L chromatography for antibody or antibody fragments having a $V_L$ kappa light chain, and affinity tags), synthetic affinity chromatography, anion/cation exchange chromatography, hydrophobic interaction chromatography, centrifugation and filtration. (Murphy et al., Antibody Technology Journal 6:17-32, 2016; Liu et al., mAbs 2(5):480-499, 2010; and Rodrigo et al., Antibodies 4:259-277, 2015.)

Antibodies Targeting IL-4Rα Loop 2

Antibodies or fragments thereof significantly binding IL-4Rα Loop 2 amino acids L42, L43, S44, and E45, and preferably not significantly binding to IL-4Rα Loop 3, can readily be obtained based on PD2-31. Techniques based on PD2-31 include affinity maturation of PD2-31 CDR's followed by screening against mutated IL-4Rα as described in the Examples below; and obtaining additional antibodies targeting IL-4Rα, carrying out competition assays with PD2-31, and confirming binding using the assays described in the Examples below. Antibodies targeting IL-4Rα can be obtained using a variety of techniques employing IL-4Rα as an immunogen in an animal (e.g., mouse, rabbit, rat, or camel) or as an antigen for phage display.

The "antibody or fragment thereof that capable of significantly binding to the Loop 2 of human IL-4Rα" or the "antibody that capable of significantly binding to Loop 2 of human IL-4Rα, but does not significantly bind to Loop 3 of human IL-4Rα, or The "fragment thereof" can be prepared by, for example, the following method: firstly an antibody against IL-4Rα (the anti-IL-4Rα antibody) or a fragment thereof is prepared by a known method; and then testing the antibody against IL-4Rα prepared and the wild type IL-4Rα or mutated IL-4Rα (such as one or more of hIL-4Rα-Mu219, 220, 241, 242, 244, 245) to determine whether the anti-IL-4Rα antibody or fragment thereof capable of significantly binding to Loop 2 of human IL-4Rα or not, or to determine the anti-IL-4Rα antibody or fragment thereof capable of significantly binding to Loop 2 of human IL-4Rα, but does not significantly bind to Loop 3 of antibody human IL-4Rα, so as to screen the antibodies that "capable of significantly binding to Loop 2 of human IL-4Rα or a fragment thereof" or "an antibody or fragment thereof that capable of significantly binding to Loop 2 of human IL-4Rα, but does not significantly bind Loop 3 of human IL-4Rα".

Treatment and Administration

IL-4Rα binding agents may be used to treat diseases mediated by IL-4 receptor complexes. IL-4Rα forms receptor complexes with the common δ chain (type I) and the IL-13 receptor (type II). Type I receptor activity is initiated by IL-4 binding leading to signal transduction, and can be inhibited by agents targeting IL-4Rα. Type II receptor activity is initiated by IL-4 or IL-13 binding leading to signal transduction, and can be inhibited by agents targeting IL-4Rα or IL-13R.

IL-4Rα binding agents can be useful for treating a disease in a patient mediated IL-4 (type I) or IL-4/IL-13 (type II) signal transduction. In one embodiment the patient has a disease selected from the group consisting of: atopic dermatitis, arthritis (including septic arthritis), herpes, chronic primary urticaria, scleroderma, hypertrophic scar, Whipple's disease, benign prostatic hyperplasia, lung diseases such as mild, moderate and severe asthma, allergic rhinitis, chronic sinusitis, hay fever, chronic obstructive pulmonary disease, and pulmonary fibrosis, eosinophilia, psoriasis, psoriatic arthritis, and inflammatory diseases such as inflammatory bowel disease, allergic reactions, Kawasaki disease, sickle cell disease, Churg-Strauss syndrome, Graves' disease, pre-eruptive purpura, Sjogren's syndrome, autoimmune lymphoproliferative syndrome, autoimmune hemolytic anemia, Barrett's esophagus, autoimmune uveitis, tuberculosis, hereditary allergic dermatitis, ulcerative colitis, fibrosis, and kidney diseases.

In other embodiments, the patient has a disease selected from the group consisting of: asthma, atopic dermatitis, eczema, sinusitis, nasal polyposis, nasal polyps, sclerosis, eosinophilic oesophagitis, allergic oesophagitis, oesophagitis, Sjogren's syndrome, chronic obstructive pulmonary disease and emphysema; the patient has asthma; or the patient has atopic dermatitis.

In other embodiments, the patient has a disease which mediated by IL-4Ra or IL-4 or IL-13 or IL-13Ra1 receptor complexes.

In other embodiments, the patient has a disease selected from the group consisting of: asthma; atopic dermatitis, eczema; rhinitis; sinusitis; nasal polyposis; eosinophilic oesophagitis, chronic obstructive pulmonary disease; food allergy; urticaria; scleroderma; idiopathic pulmonary, fibrosis; pemphigoid; and pruritus.

Atopic dermatitis is a chronic, reoccurring pruritic inflammatory skin disease. Atopic dermatitis is commonly associated asthma and allergic rhinitis. IL-4Rα binding agents can be used as a standalone therapy for treating atopic dermatitis, or can be used in combination with one or more additional treatments. Existing treatments for atopic dermatitis include topical corticosteroids, topical calcineurin inhibitors, antimicrobial therapy (for patients with accompanying bacterial infections), antihistamine therapy, phosphodiesterase inhibitors, phototherapy, crisaborole, and Dupilumab. (Maliyar et al., Advances in Skin and Wound Care 31(12):538-550, 2018.)

Asthma is an obstructive lung disease, and can be classified as intermittent, mild, moderate and severe persistent. IL-4Rα binding agents can be used as a standalone therapy for treating asthma, or can be used in combination with one or more treatments. Existing treatments include beta-2 agonists (e.g., albuterol, levalbuterol, terbutaline, metaproterenol, pirbuterol, salmeterol, and formoterol), corticosteroids (e.g., beclomethasone, triamcinolone, flunisolide, ciclesonide, budesonide, fluticasone, and mometasone), leukotriene receptor antagonists and synthesis inhibitor (e.g., zafirlukast, montelukast and zileuton), antimuscarinics (e.g., ipratropium, tiotropium, aclidinium, umeclidinium and glycopyrronium), biologics (e.g., Omalizumab, Mepolizumab, Reslizumab, Benralizumab, Dupilumab, and Tezepelumab) and bronchial thermoplasty. In different embodiments, the asthma patient has intermittent, mild, moderate or severe persistent asthma. (So et al., EMJ 3(4):111-121, 2018.)

Disease treatment is facilitated using a therapeutically effective amount of an IL-4Rα binding agent. A therapeutically effective amount is an amount sufficient to bring about a clinically meaningful reduction in one or more symptoms of the indicated disease in a patient.

IL-4Rα binding agents can be administered by different routes including parenteral injection (intravenous, subcutaneous, intramuscular or intradermal), oral, and mucosal. Subcutaneous injection generally is the chosen route. (Awwad and Angkawinitwong Pharmaceutics 10, 83, 2018.)

Optimal doses and dosing regimens can be determined taking into account different factors including efficacy of the therapeutic agent, the disease being treated, the age of the patient, the condition of the patient, the weight of patient, the sex of the patient, the route of administration and the desired effect. In different embodiments a single dose is between: about 0.05 mg/kg to about 20 mg/kg; about 0.50 mg/kg to about 15 mg/kg; or about 1 mg/kg to 10 mg/kg. Further embodiments concerning dosage include a single dose at about 10 mg, about 50 mg, about 100 mg, about 200 mg, about 300 mg, about 400 mg, about 500 mg, about 600 mg, about 700 mg, about 800 mg, about 900 mg, and about 1,000 mg. Reference to "single dose" refers to the timing of dose. Depending on the size of the dose, it may be preferable to administer a signal dose as two separate administrations provided to the patient at about the same time. Dosing regimens can provide for different times between dosing, such as one or more times a day, one or more times a week, once weekly, biweekly, and monthly or longer. The same dose need not be given each time. For example, the patient can be started off with a higher dose, followed by a lower dose; or started with a lower dose followed by a higher dose. Depending upon the effectiveness and side effects of a given dose in a patient, the dose timing and amount can be adjusted.

Administration of IL-4Rα binding agents is facilitated through the use of a pharmaceutical acceptable carrier. Preferred pharmaceutical acceptable carriers facilitate stabilization and administration of the IL-4Rα binding agents described herein. Common carrier excipients that may be present include carbohydrates, amino acids, buffering salts, and surfactants. Examples of common excipients include polysorbate 80, polysorbate 20, poloxamer 188, sucrose, trehalose, NaCl, arginine, glycine, phosphate, citrate, acetate and histidine. Suitable formulations can be optimized using consideration and techniques well known in the art. (See, e.g., Kang et al., Rapid Formulation Development for Monoclonal Antibodies, April 2016 retrieved from https://bioprocessintl.com/manufacturing/formulation/rapid-formulation-development-for-mon oclonal-antibodies/; Razinkov et al., Journal of Biomolecular Screening 20(4): 468-483, 2015; and Awwad and Angkawinitwong, Pharmaceutics 10, 83, 2018.)

Marmoset Animal Model

The ability of PD2-31 to bind to marmoset IL-4Rα at a high affinity provides for several advantages including: enabling the use of marmosets in studies evaluating pre-clinical efficacy of PD2-31 for a disease mediated by IL-4/IL-13 signal transduction; enabling the use of marmosets as a pre-clinical model for evaluating the efficacy of an antibody targeting hIL-4Rα in combination with other agents; and facilitating toxicology and safety studies. The use of marmosets as a respiratory model and a model for human allergic asthma is illustrated in Curths et al., Vet. Sci. 1:63-76, 2014 and Curths et al. Am. J. Respir. Crit. Care Med. 193:2016:A4919 (Curths A4919).

In studies evaluating the efficacy of PD2-31, or a combination treatment, appropriate stimuli and end points can be selected based on the particular disease. For example, Curths et al. A4919, illustrates marmosets as a model for human allergic asthma by sensitizing using house dust mite allergen and measuring the impact of a therapeutic agent (budesonide) on eosinophil levels. Depending on the particular disease other stimuli and end-points can be employed.

EXAMPLES

Hereinafter, the present invention is described in more detail by way of examples. It should be understood that the present application is not limited to these examples.

Example 1. Preparation of the Monoclonal Antibodies Against Human Interleukin-4 Receptor Alpha The human interleukin-4 receptor alpha (IL-4Rα) was purchased from Shanghai Novoprotein Technology Co., Ltd. for immunizing New Zealand rabbits. The antigen-binding specific antibody clones were obtained by using B cell cloning technology, and then screened for the monoclonal antibody that binds to IL-4Rα and has the IL-4 and/or IL-13 inhibitory activity. First, the cell supernatant was detected by binding ELISA and clones that bind to IL-4Rα were selected; and then clones with the IL-4/IL-13 inhibitory activity were selected by detection using the HEK Blue™ IL-4/IL-13 reporter gene cell system (InvivoGen). The above immunization and screening process was entrusted to a commercial company for completion.

Sixteen clones were selected for recombinant expression and sequencing. Affinity maturation and humanization were performed on the #2 and #82 clones. The homology alignment to human IgG germline sequences was performed using NCBI IgBlast. IGHV3-66*01 was selected as the template for heavy chain CDR grafting, and the heavy chain CDR regions (i.e., CDR-H1 (SEQ ID NO: 1), CDR-H2 (SEQ ID NO: 2), and CDR-H3 (SEQ ID NO: 3)) of the #2 clone were grafted into the framework regions of IGHV3-66*01. IGKV1-39*01 was selected as the template for light chain CDR grafting, and the light chain CDR regions (i.e., CDR-L1 (SEQ ID NO: 4), CDR-L2 (SEQ ID NO: 5), and CDR-L3 (SEQ ID NO: 6)) of the #2 clone were grafted into the framework regions of IGKV1-39*01. Back mutation was performed at specific sites in the framework regions to obtain the variable regions of the monoclonal antibody PD2-31 of the present invention. Finally, the amino acid sequence of the humanized heavy chain variable region is set forth in SEQ ID NO: 7; and the amino acid sequence of the humanized light chain variable region is set forth in SEQ ID NO: 8.

Alternatively, the homology alignment to human IgG germline sequences was performed using NCBI IgBlast. IGHV3-66*01 was selected as the template for heavy chain CDR grafting, and the heavy chain CDR regions (i.e., CDR-H1 (SEQ ID NO: 14), CDR-H2 (SEQ ID NO: 15), and CDR-H3 (SEQ ID NO: 16)) of the #82 clone were grafted into the framework regions of IGHV3-66*01. IGKV1-39*01 was selected as the template for light chain CDR grafting, and the light chain CDR regions (i.e., CDR-L1

(SEQ ID NO: 17), CDR-L2 (SEQ ID NO: 18), and CDR-L3 (SEQ ID NO: 19)) of the #82 clone were grafted into the framework regions of IGKV1-39*01. Back mutation was performed at specific sites in the framework regions to obtain the variable regions of the monoclonal antibody HZD82-12 of the present invention. Finally, the amino acid sequence of the humanized heavy chain variable region is set forth in SEQ ID NO: 12; and the amino acid sequence of the humanized light chain variable region is set forth in SEQ ID NO: 13.

The gene of the above heavy chain variable region (SEQ ID NO: 7) was artificially synthesized and inserted into the pUC57 vector; and the gene of the above light chain variable region (SEQ ID NO: 8) was obtained by PCR amplification. The gene of the heavy chain variable region and the heavy chain expression plasmid pHZDCH were digested with HindIII and NheI. The gene of the light chain variable region and the light chain expression plasmid pHZDCK were digested with HindIII and BsiWI. The T4 DNA ligase was used to insert the digested fragments into the corresponding expression plasmids, respectively, and the heavy chain expression plasmid pHZDCH-2VH-Hu1 and the light chain expression plasmid pHZDCK-2VK-pd18 were constructed.

The gene of the above heavy chain variable region (SEQ ID NO: 12) was obtained by PCR amplification; and the gene of the light chain variable region (SEQ ID NO: 13) was artificially synthesized and inserted into the pUC57 vector. The gene of the heavy chain variable region and the heavy chain expression plasmid pHZDCH were digested with HindIII and NheI. The gene of the light chain variable region and the light chain expression plasmid pHZDCK were digested with HindIII and BsiWI. The T4 DNA ligase was used to insert the digested fragments into the corresponding expression plasmids, respectively, and the heavy chain expression plasmid pHZDCH-82VH-Hu3 and the light chain expression plasmid pHZDCK-82VK-Hu1 were constructed.

Figure 1B:
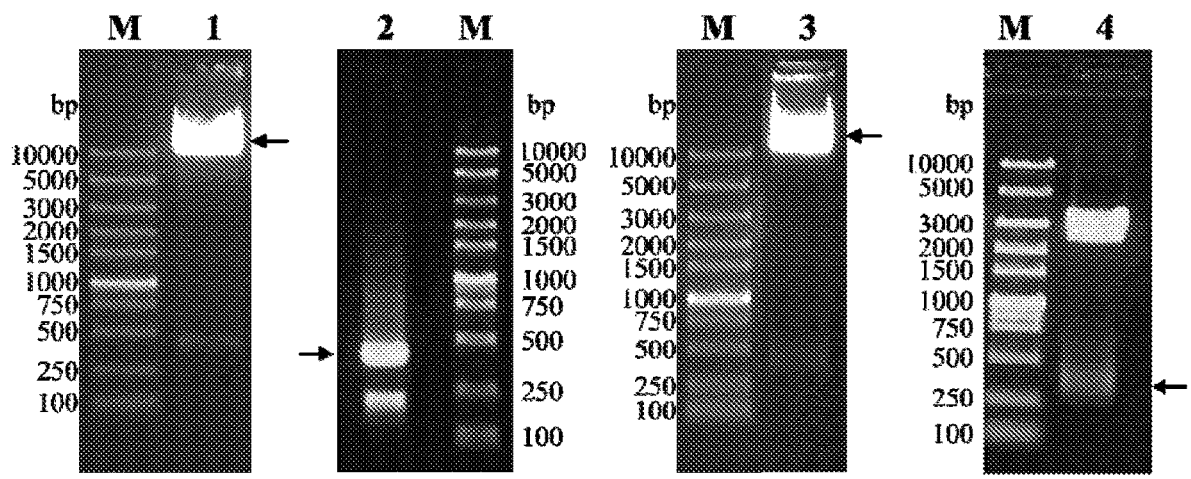

The results of double digestion of the plasmids were detected by nucleic acid electrophoresis. The results of double digestion of the heavy chain variable region and the light chain variable region of the antibody as well as the heavy and light chain expression plasmids can be seen from the results in FIG. 1(A), wherein the heavy and light chain plasmids are about 10,000 bp, the light chain variable region is about 408 bp, and the heavy chain variable region is about 429 bp. The results of double digestion of the heavy chain variable region and the light chain variable region of the antibody as well as the heavy and light chain expression plasmids can be seen from the results in FIG. 1(B), wherein the heavy and light chain plasmids are about 10,000 bp, the light chain variable region is about 408 bp, and the heavy chain variable region is about 426 bp.

Figure 2:
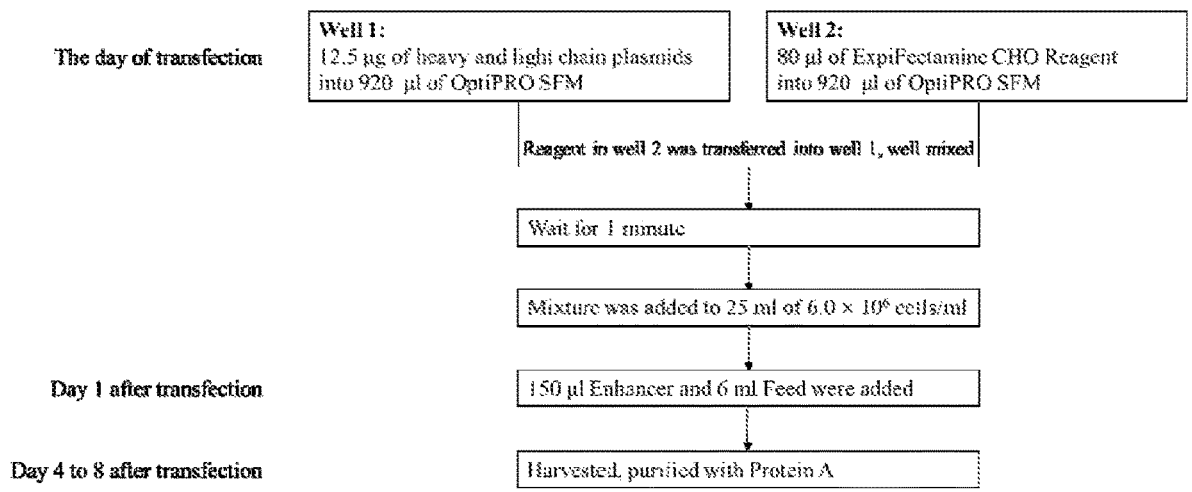
FIG. 2 is a flow chart of the transient expression.

The heavy chain expression plasmid and the light chain expression plasmid with correct sequences were co-transfected into ExpiCHO-S cells. One day before transfection, the ExpiCHO-S cells were diluted to $3\times10^6$ cells/ml for pre-transfection sub-culturing. On the day of transfection, the cells were diluted to the density of $6\times10^6$ cells/ml, and 25 ml of cells was placed into a 125 ml shake flask until transfection. The transfection and expression process was as shown in FIG. 2.

Figure 3A:
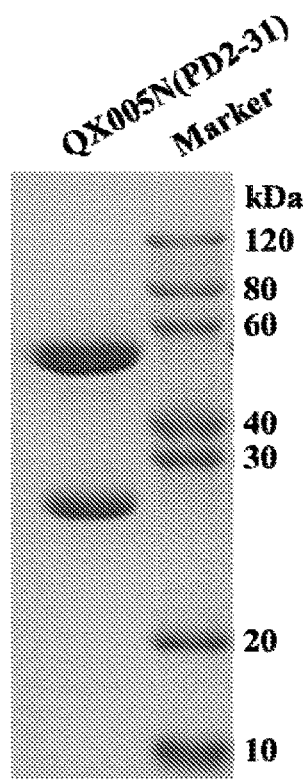
FIG. 3(A)-3(B) are graphs showing the results of protein electrophoresis.
Figure 3B:
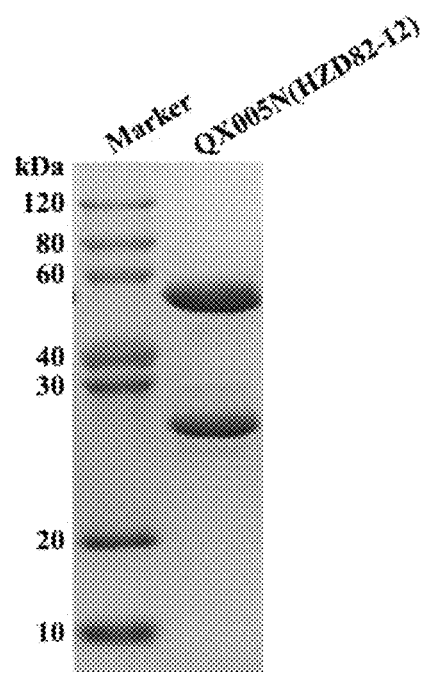

On day 4 to 8 after transfection, the culture supernatant was harvested and further purified with Protein A. The purified antibodies were detected by SDS-PAGE electrophoresis and named as QX005N (specifically QX005N (PD2-31) and QX005N (HZD82-12), respectively). The results of detecting the antibodies by protein electrophoresis are shown in FIGS. 3(A) and 3(B). The protein electrophoresis was performed on a denatured reducing gel. The results in FIG. 3(A) show two bands with sizes of approximately 50 kDa and 25 kDa, respectively, which are consistent with the theoretical molecular weights of the heavy chain (48.5 kDa) and the light chain (23.7 kDa). The results in FIG. 3(B) show two bands with sizes of approximately 50 kDa and 25 kDa, respectively, which are consistent with the theoretical molecular weights of the heavy chain (48.3 kDa) and the light chain (23.6 kDa).

Example 2. Determination of the Equilibrium Dissociation Constant ($K_D$)

The affinity of the monoclonal antibodies PD2-31, HZD82-12 and Dupilumab for human IL-4Rα (Shanghai Novoprotein Technology Co., Ltd) was detected by Biacore T200, and all the procedures were carried out at 25° C. The protein A was chemically coupled to a CM5 chip, and an appropriate amount of the antibody was immobilized by a capture method such that the Rmax was less than 50 RU and the flow rate for the capture was 10 μl/min. The antigen was subject to gradient dilution, and the flow rate in the instrument was switched to 30 μl/min. The antigen was flowed through the reference channel and the channel with the immobilized antibody sequentially in an ascending order of concentration, and the running buffer was flowed through as a negative control. After each binding and dissociation was complete, the chip was regenerated with glycine, pH 1.5. Fitting was performed with the build-in software in the instrument according to a 1:1 binding model. The binding rate constant $k_a$, the dissociation rate constant $k_d$, and the equilibrium dissociation constant $K_D$ values of the antibody were calculated. Dupilumab was obtained by purchasing a commercially available medicine.

The results are shown in Table 1.

TABLE 1

| The affinity of antibodies binding to human hIL-4Rα | | | |
|---|---|---|---|
| Sample name | $k_a$ ($10^5$ $M^{-1}S^{-1}$) | $k_d$ ($10^{-4}$ $S^{-1}$) | $K_D$ ($10^{-10}$M) |
| PD2-31 | 6.12 | 2.36 | 3.78 |
| HZD82-12 | 4.81 | 0.99 | 2.07 |
| Dupilumab | 8.08 | 1.10 | 1.36 |

Data in the table are those obtained by calculating the average value with each sample detected twice.

Example 3. Determination of Binding to Marmoset IL-4Rα

Binding of monoclonal antibodies PD2-3 and Dupilumab to marmoset IL-4Rα was studied by Biacore T200, according to the methods in Example 2. Marmoset IL-4Rα was prepared—by standard techniques. Briefly, the expression plasmid containing the extracellular domain of marmoset IL-4Rα (Accession #QOPIT7) was constructed and transfected into HEK 293F cells. After expression, the extracellular domain of marmoset IL-4Rα (Gly 24-His 232) with C-terminus his-tag was purified by Nickel chromatography.

The $K_D$ value of PD2-31 binding to marmoset IL-4Rα is about 100 pM. The results show that PD2-31 binds to marmoset IL-4Rα to the same extent as it binds to human IL-4Rα. Dupilumab doesn't bind to marmoset IL-4Rα, and thus recognizes a different epitope than PD2-31.

Example 4. PD2-31 Binds to Different Mutated hIL-4Rα

To further narrow down the key amino acids that PD2-31 binds to, multiple mutants of hIL-4Rα were designed in Loop 2 (V40FLLSEA46) and Loop 3 (M65DDVVSADN73) (Table 2). The wild-type hIL-4Rα (hIL-4Rα-ECD) and hIL-4Rα mutants were prepared using standard techniques. Briefly, the expression plasmids containing the extracellular domain of wild-type hIL-4Rα and different mutated hIL-4Rα were constructed and transfected into HEK 293F cells. After expression, the extracellular domain of wild-type hIL-4Rα and hIL-4Rα mutants with C-terminus his-tag were purified by Nickel chromatography. Purified proteins of wild-type hIL-4Rα and hIL-4Rα mutants were analyzed for interaction with PD2-31 and Dupilumab. The interaction was studied by Biacore T200, according to the methods in Example 2. The results are shown in table 2.

TABLE 2

The affinity of antibodies binding to wild-type hIL-4Rα and different hIL-4Rα mutants

| | | | PD2-31 | | | Dupilumab | | |
| --- | --- | --- | --- | --- | --- | --- | --- | --- |
| Name | Mutation | Location | ka (1/Ms) | kd (1/s) | KD (M) | ka (1/Ms) | kd (1/s) | KD (M) |
| hIL-4Rα-ECD | | | 7.79E+05 | 1.34E−04 | 1.69E−10 | 7.07E+05 | 4.29E−05 | 5.88E−11 |
| hIL-4Rα-Mu219 | L42Q/L43S/S44L | Loop 2 | | N/A | | | N/A | |
| hIL-4Rα-Mu220 | L43S/S44L/E45K | | | N/A | | | N/A | |
| hIL-4Rα-Mu239 | M65I/D66A/D67A | Loop3 | 1.66E+05 | 2.71E−05 | 1.63E−10 | 2.53E+05 | 5.63E−05 | 2.23E−10 |
| hIL-4Rα-Mu240 | D66A/D67A/V68R | | 6.98E+04 | 5.23E−05 | 7.50E−10 | 1.03E+05 | 4.21E−04 | 4.07E−09 |
| hIL-4Rα-Mu241 | D67A/V68R/V69F | | 1.39E+05 | 6.59E−05 | 4.74E−10 | 1.08E+05 | 4.44E−03 | 4.12E−08 |
| hIL-4Rα-Mu242 | V68R/V69F/S70Q | | 1.41E+05 | 1.38E−04 | 9.79E−10 | 1.31E+05 | 3.57E−03 | 2.73E−08 |
| hIL-4Rα-Mu243 | V69F/S70Q/A71L | | 7.23E+05 | 9.45E−05 | 1.31E−10 | 9.45E+05 | 3.41E−05 | 3.61E−11 |
| hIL-4Rα-Mu244 | S70Q/A71L/D72R | | 9.45E+04 | 1.04E−04 | 1.10E−09 | | N/A | |
| hIL-4Rα-Mu245 | A71L/D72R/N73A | | 2.01E+05 | 2.90E−04 | 1.45E−09 | | N/A | |
| hIL-4Rα-Mu453 | D66A/D67A | | 1.78E+05 | 1.18E−04 | 6.63E−10 | 1.93E+05 | 3.78E−05 | 1.96E−10 |

The results of hIL-4Rα-ECD are mean value of three different experiments.
"N/A" means the $K_D$ value of antibody is too low to be measured precisely by Biacore T200.

The $K_D$ values of PD2-31 binding to hIL-4Rα-Mu219 and hIL-4Rα-Mu220 are too low to be measured precisely, and the $K_D$ values of PD2-31 binding to 8 different Loop3-mutated hIL-4Rα (i.e., hIL-4Rα-Mu239, hIL-4Rα-Mu240, hIL-4Rα-Mu241, hIL-4Rα-Mu242, hIL-4Rα-Mu243, hIL-4Rα-Mu244, hIL-4Rα-Mu245 and hIL-4Rα-Mu453 in the table 2) are about or less than 1 nM. The above results indicate that PD2-31 binds to amino acids in Loop 2, especially capable of binding the L42, L43, S44, and E45 in Loop 2 of the hIL-4Rα; but does not appear to bind amino acids 65-73 of Loop 3, especially no significant binding to the M65, D66, D67, V68, V69, S70, A71, D72 and N73 in Loop 3 of the hIL-4Rα.

The $K_D$ values of Dupilumab binding to hIL-4Rα-Mu219 and hIL-4Rα-Mu220 are too low to be measured precisely, and the $K_D$ values of Dupilumab binding to hIL-4Rα-Mu241, hIL-4Rα-Mu242, hIL-4Rα-Mu244 and hIL-4Rα-Mu245 are higher than 10 nM. The above results indicate that Dupilumab binds to amino acids located in Loop 2 and Loop 3.

The alignment results between human and marmoset IL-4Rα and the loop regions are shown in the FIG. 10(A) and FIG. 10(B).

In the specification, if the $K_D$ of antibody binding to mutated hIL-4Rα is increased less than 10 times of the $K_D$ of wild-type hIL-4Rα, it means the binding activity of antibody is not reduced by these sites' mutations, and these mutated sites are not the epitope of antibody, and means the antibody does not significantly bind to these amino acids. If the $K_D$ of antibody binding to mutated hIL-4Rα is increased 10 times or more higher than that of wild-type hIL-4Rα, it means the binding activity of antibody is significantly changed by these sites' mutations, and which indicates that the binding activity of antibody is significantly changed, and means the antibody significantly binds these amino acids.

Figure 4A:
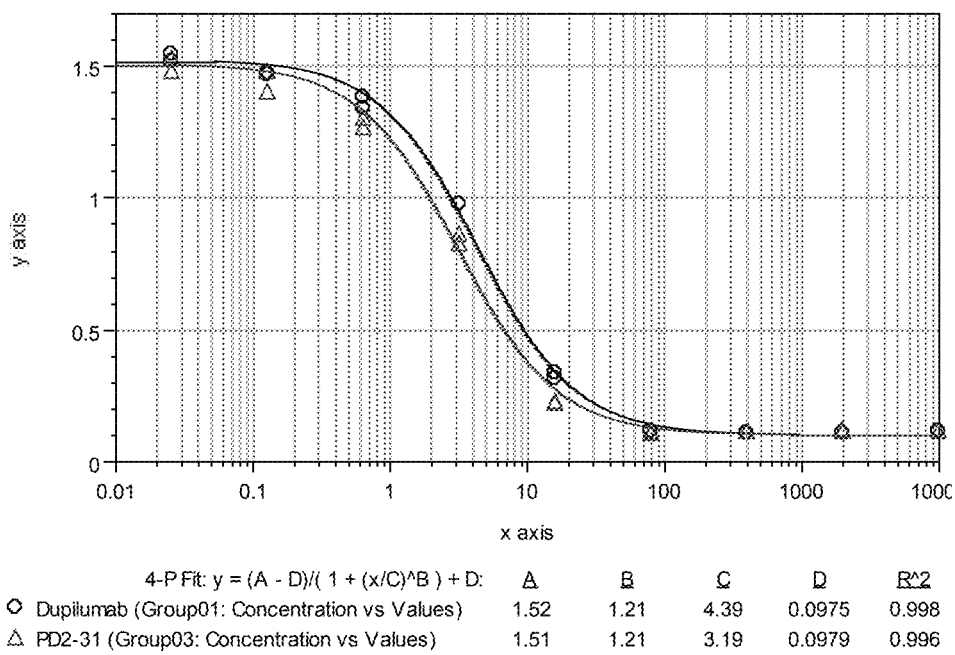
FIG. 4(A)-4(D) are graphs showing that QX005N inhibits the IL-4- or IL-13-induced STAT6 phosphorylation activity in HEK Blue™ IL-4/IL-13 cells.
Figure 4B:
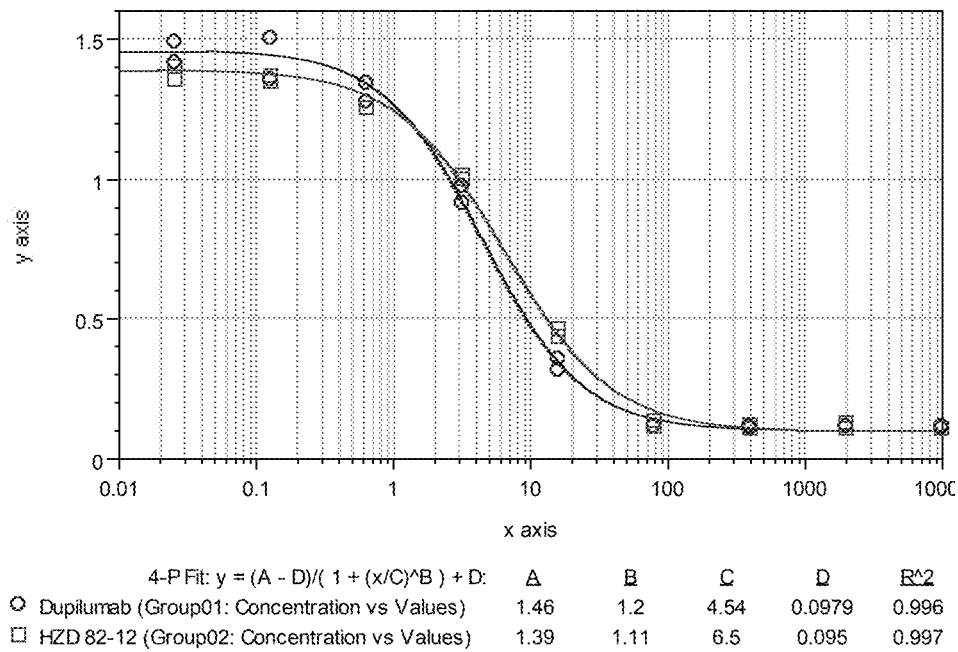
Figure 4C:
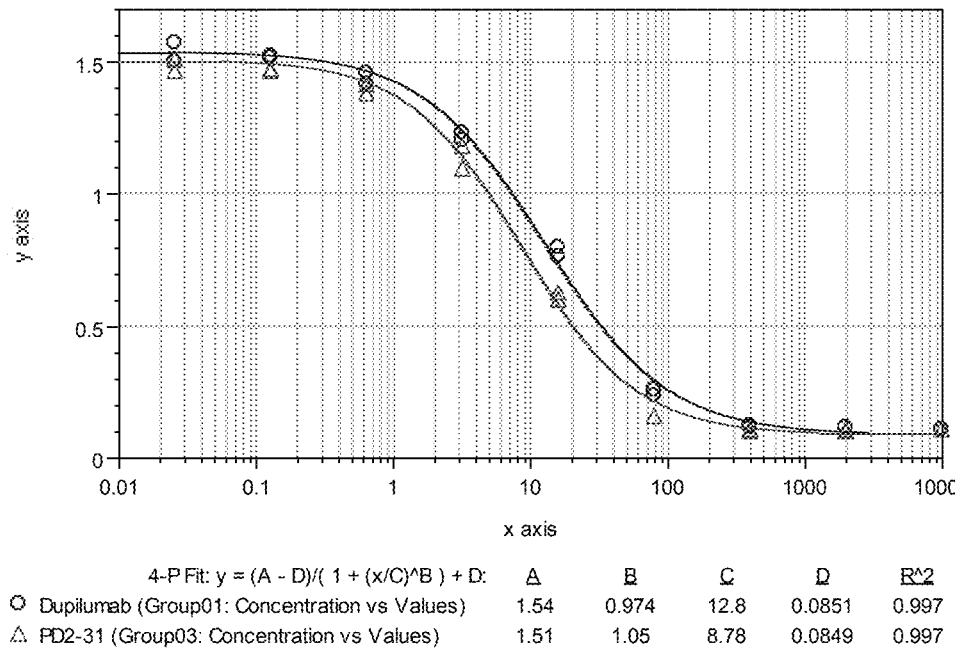
Figure 4D:
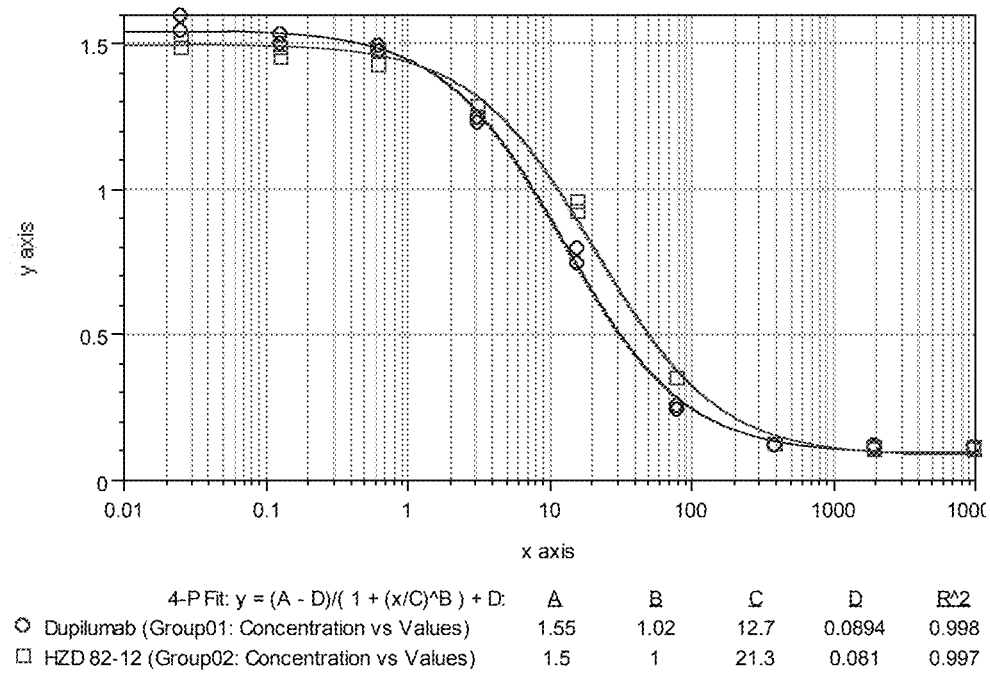

Example 5. Inhibition of the IL-4- and IL-13-Induced STAT6 Phosphorylation Activity in the HEK Blue™ IL-4/IL-13 Cells The HEK Blue™ IL-4/IL-13 reporter gene cell line was used to determine the ability of monoclonal antibodies PD2-31 and HZD82-12 to antagonize the intracellular signaling molecule STAT6 phosphorylation activity mediated by IL-4/IL-13 via IL-4Rα. The cells in culture were added to 96 wells at $4 \times 10^4$ cells per well, and then cultured overnight under the conditions of 37° C. and 5% $CO_2$. Serial dilutions with antibody concentrations ranging from 0 to 10 ug/ml were added to the cells, and 0.2 ng/ml of IL-4 or 20 ng/ml of IL-13 was added. Then, the cells were cultured for 24 hours under the conditions of 37° C. and 5% $CO_2$. The cell culture supernatant was collected and reacted with 10% QUANTI-Blue™ detection reagent under the conditions of 37° C. and 5% $CO_2$ for 1 hour. Then, the $OD_{630\,nm}$ value was detected and the dose-response curve was plotted (FIGS. 4(A)-4(D)) to analyze the antagonistic activity of the antibody. The results show that both monoclonal antibodies are capable of inhibiting the IL-4- and IL-13-induced STAT6 phosphorylation in the HEK Blue™ IL-4/IL-13 cells. FIG. 4(A) shows the results indicating that PD2-31 inhibits the IL-4-induced STAT6 phosphorylation activity in the HEK Blue™ IL-4/IL-13 cells. It can be seen from the results in FIG. 4(A) that PD2-31 and Dupilumab inhibit the IL-4-induced STAT6 phosphorylation activity in the HEK Blue™ IL-4/IL-13 cells with an $IC_{50}$ of 3.19 ng/ml and 4.39 ng/ml, separately. FIG. 4(B) shows the results indicating that HZD82-12 inhibits the IL-4-induced STAT6 phosphorylation activity in the HEK Blue™ IL-4/IL-13 cells. It can be seen from the results in FIG. 4(B) that HZD82-12 and Dupilumab inhibit the IL-4-induced STAT6 phosphorylation activity in the HEK Blue™ IL-4/IL-13 cells with an $IC_{50}$ of 6.5 ng/ml and 4.54 ng/ml, separately. FIG. 4(C) shows the results indicating that PD2-31 inhibits the IL-13-induced STAT6 phosphorylation activity in the HEK Blue™ IL-4/IL-13 cells. It can be seen from the results in FIG. 4(C) that PD2-31 and Dupilumab inhibit the IL-13-induced STAT6 phosphorylation activity in the HEK Blue™ IL-4/IL-13 cells with an $IC_{50}$ of 8.78 ng/ml and 12.8 ng/ml, separately. FIG. 4(D) shows the results indicating that HZD82-12 inhibits the IL-13-induced STAT6 phosphorylation activity in the HEK Blue™ IL-4/IL-13 cells. It can be seen from the results in FIG. 4(D) that HZD82-12 and Dupilumab inhibit the IL-13-induced STAT6 phosphorylation activity in the HEK Blue™ IL-4/IL-13 cells with an $IC_{50}$ of 21.3 ng/ml and 12.7 ng/ml, separately.

Figure 5A:
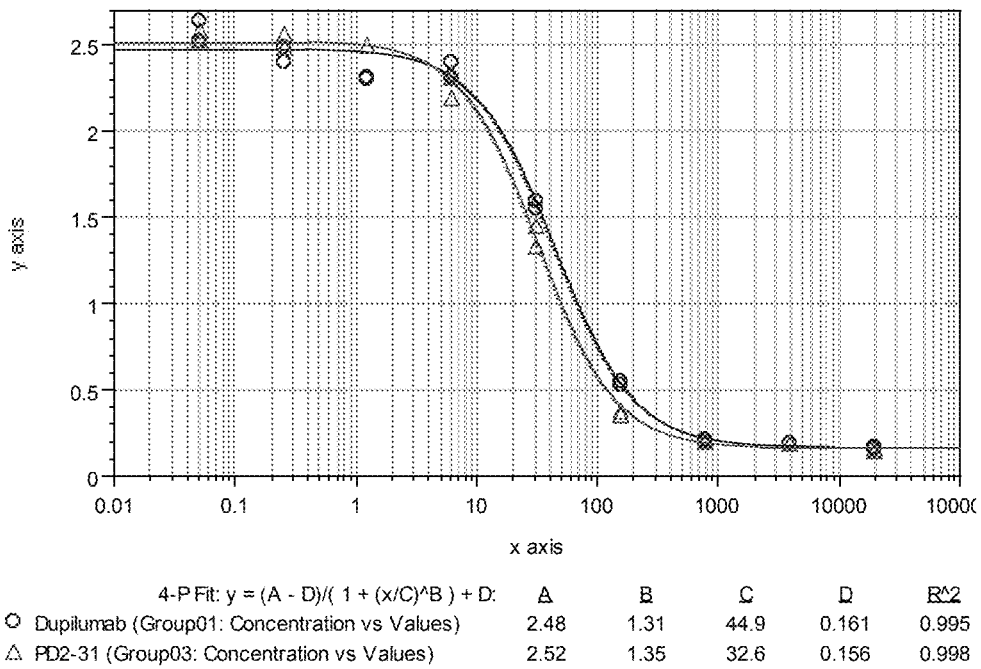
FIG. 5(A)-5(D) are graphs showing that QX005N inhibits the IL-4- or IL-13-induced CCL-17 release activity in A549 cells.
Figure 5B:
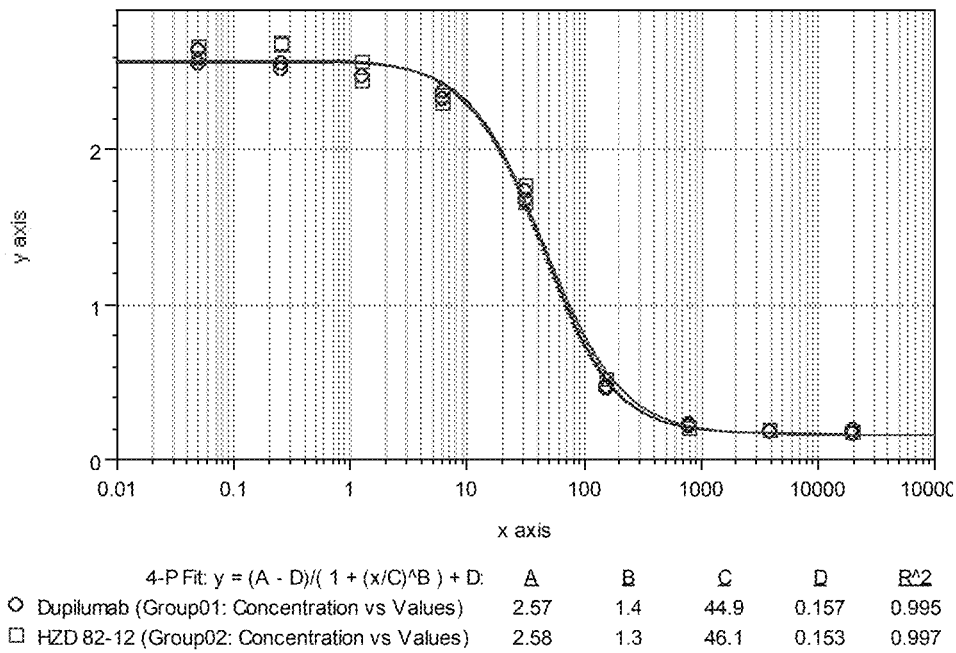
Figure 5C:
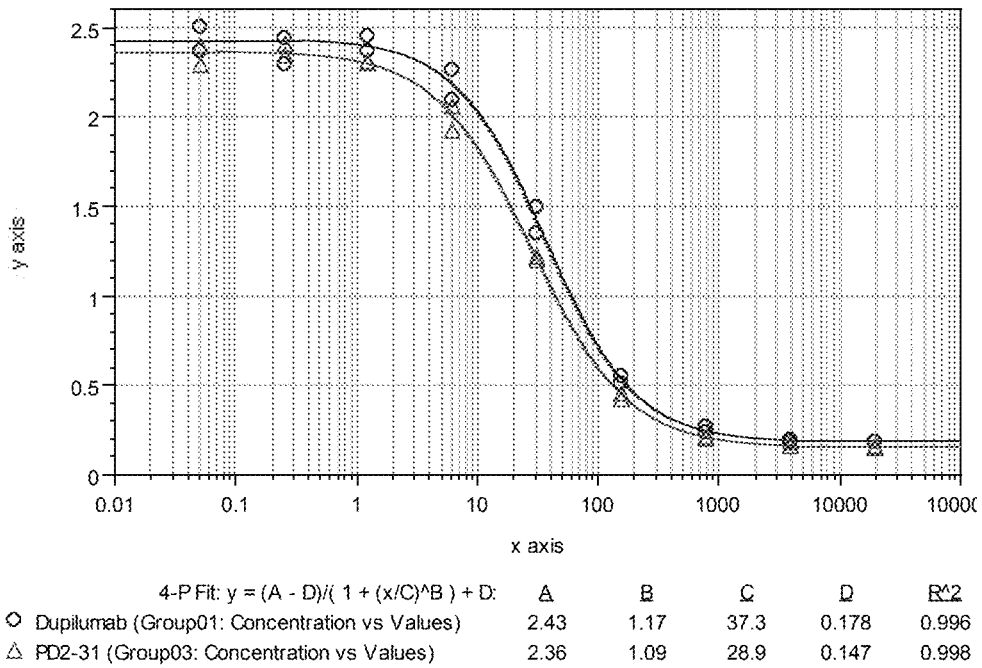
Figure 5D:
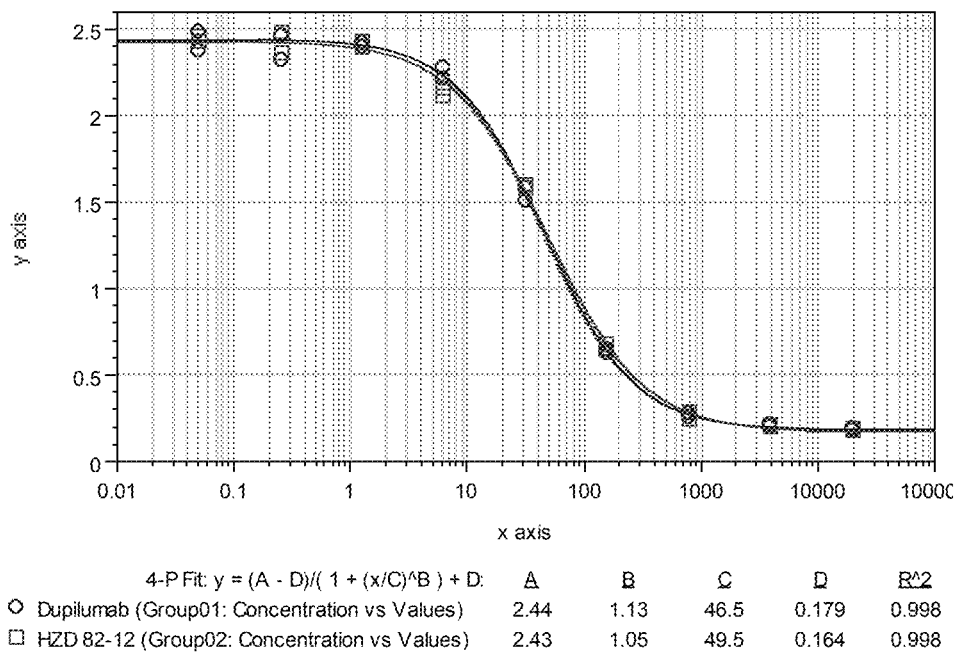

Example 6. Inhibition of the IL-4- and IL-13-Induced CCL-17 Release Activity in the A549 Cells The A549 human lung cancer epithelial cell line was used to determine the ability of monoclonal antibodies PD2-31 and HZD82-12 to antagonize the CCL-17 release activity mediated by IL-4/IL-13 via IL-4Rα. The cells in culture were added to 96 wells at $3 \times 10^4$ cells per well, and then cultured overnight under the conditions of 37° C. and 5% $CO_2$. Serial dilutions with antibody concentrations ranging from 0 to 20 ug/ml were added to the cells, and 20 ng/ml of TNF-α and 1 ng/ml of IL-4 or 20 ng/ml of IL-13 were added. Then, the cells were cultured for 24 hours under the conditions of 37° C. and 5% $CO_2$. The cell culture supernatant was collected. The expression of CCL-17 in the supernatant was detected by the sandwich ELISA method and the dose-response curve was plotted (FIGS. 5(A)-5(D)) to analyze the antagonistic activity of the antibody. The results show that the antibodies are capable of inhibiting the IL-4- and IL-13-induced CCL-17 release in the A549 cells. FIG. 5(A) shows the results indicating that PD2-31 inhibits the IL-4-induced CCL-17 release activity in the A549 cells. It can be seen from the results in FIG. 5(A) that PD2-31 and Dupilumab inhibit the IL-4-induced CCL-17 release activity in the A549 cells with an $IC_{50}$ of 32.6 ng/ml and 44.9 ng/ml, separately. FIG. 5(B) shows the results indicating that HZD82-12 inhibits the IL-4-induced CCL-17 release activity in the A549 cells. It can be seen from the results in FIG. 5(B) that HZD82-12 and Dupilumab inhibit the IL-4-induced CCL-17 release activity in the A549 cells with an $IC_{50}$ of 46.1 ng/ml and 44.9 ng/ml, separately. FIG. 5(C) shows the results indicating that PD2-31 inhibits the IL-13-induced CCL-17 release activity in the A549 cells. It can be seen from the results in FIG. 5(C) that PD2-31 and Dupilumab inhibit the IL-13-induced CCL-17 release activity in the A549 cells with an $IC_{50}$ of 28.9 ng/ml and 37.3 ng/ml, separately. FIG. 5(D) shows the results indicating that HZD82-12 inhibits the IL-13-induced CCL-17 release activity in the A549 cells. It can be seen from the results in FIG. 5(D) that HZD82-12 and Dupilumab inhibit the IL-13-induced CCL-17 release activity in the A549 cells with an $IC_{50}$ of 49.5 ng/ml and 46.5 ng/ml, separately.

Figure 6A:
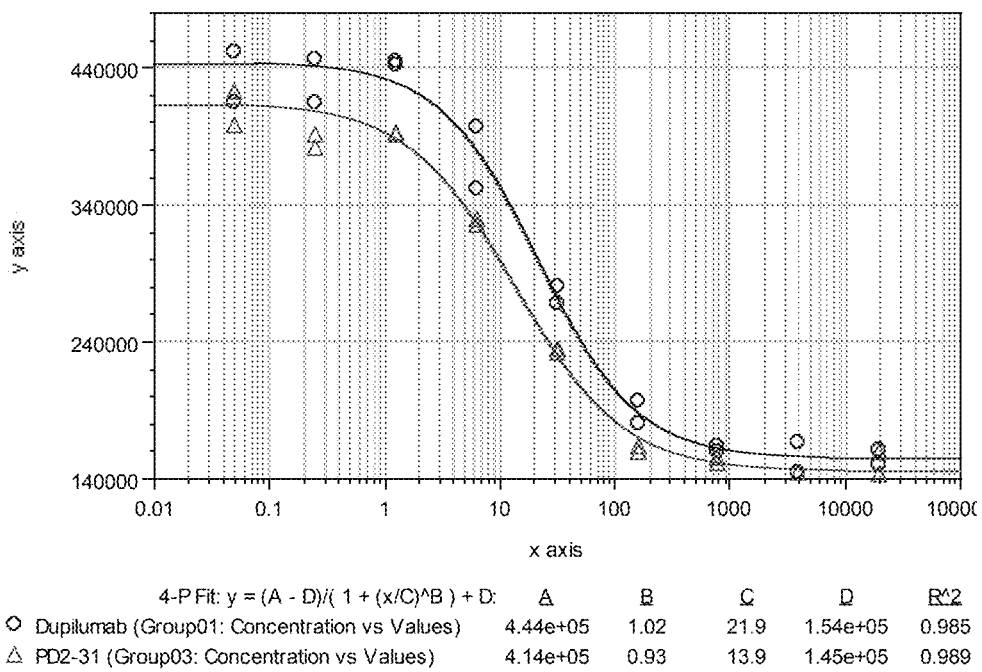
FIG. 6(A)-6(D) are graphs showing that QX005N inhibits the IL-4- or IL-13-induced proliferation activity of TF-1 cells.
Figure 6B:
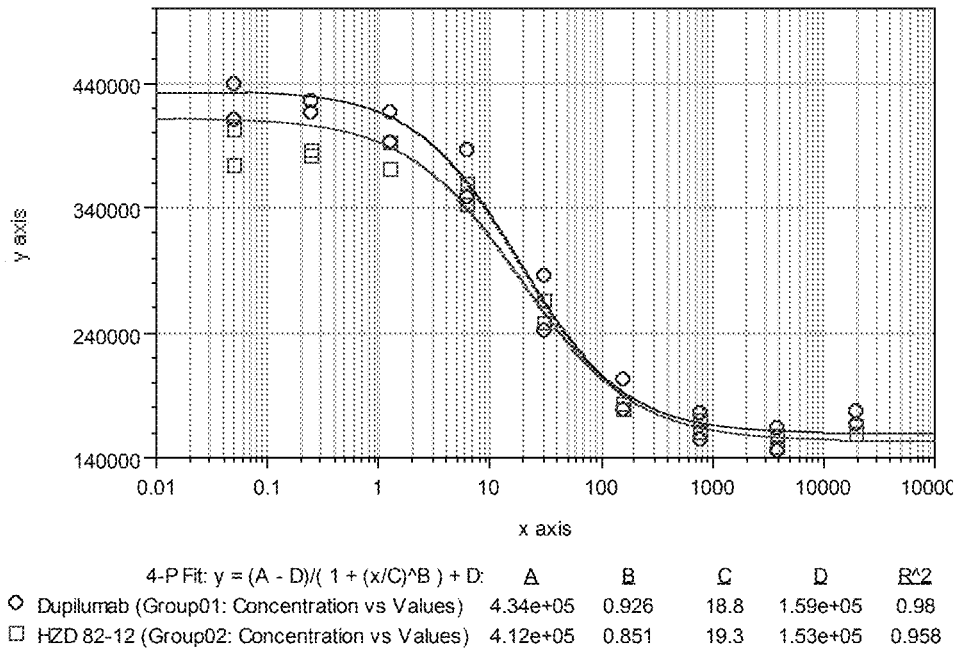
Figure 6C:
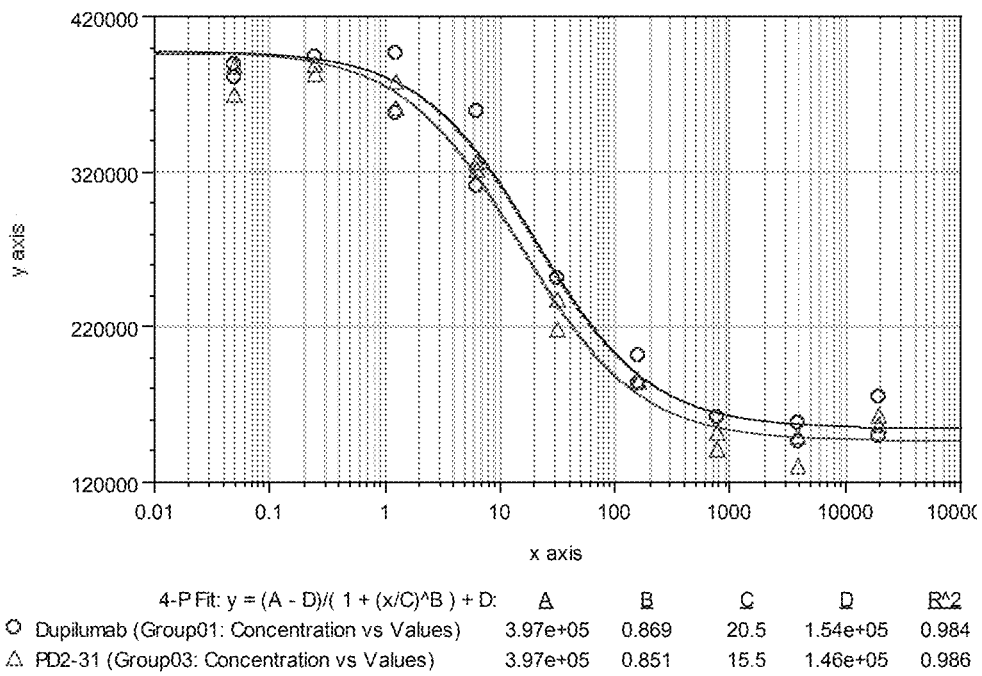
Figure 6D:
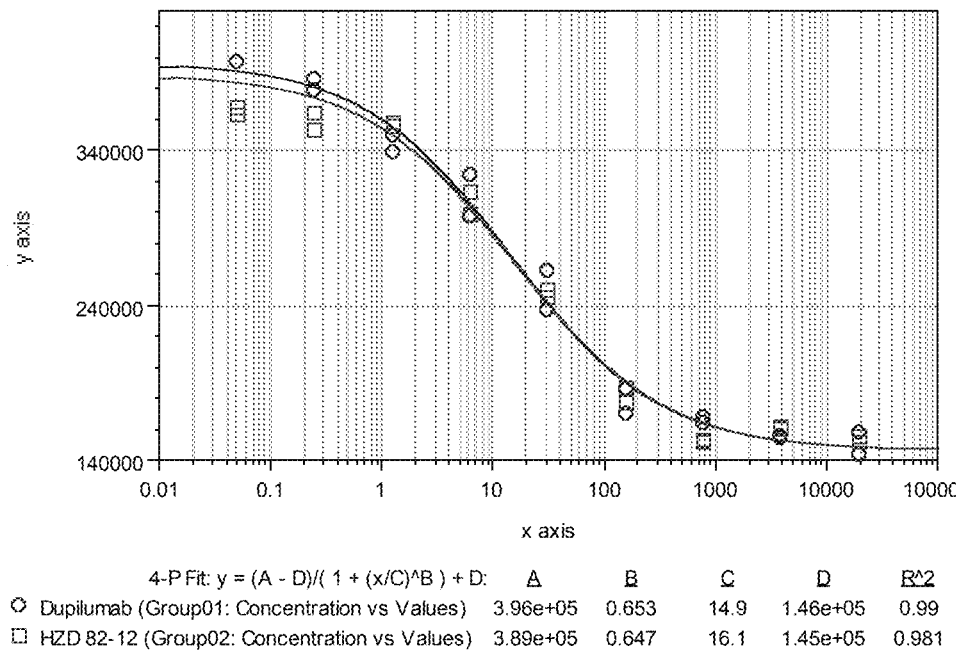

Example 7. Inhibition of the IL-4- and IL-13-Induced Proliferation Activity of the TF-1 Cells The TF-1 human erythroid leukemia cell line was used to determine the ability of PD2-31 and HZD82-12 to antagonize the cell proliferation activity mediated by IL-4/IL-13 via IL-4Rα. The cells in culture were added to 96 wells at $2 \times 10^4$ cells per well, and then cultured overnight under the conditions of 37° C. and 5% $CO_2$. Serial dilutions with antibody concentrations ranging from 0 to 20 µg/ml were added to the cells, and 1 ng/ml of IL-4 or 20 ng/ml of IL-13 was added. Then, the cells were cultured for 72 hours under the conditions of 37° C. and 5% $CO_2$. The cell culture was collected. The cell proliferation status was detected by the CellTiter-Glo assay and the dose-response curve was plotted (FIGS. 6(A)-6(D)) to analyze the antagonistic activity of the antibody. The results show that the antibodies are capable of inhibiting the IL-4- and IL-13-induced proliferation of the TF-1 cells. FIG. 6(A) shows the results indicating that PD2-31 inhibits the IL-4-induced proliferation activity of the TF-1 cells. It can be seen from the results in FIG. 6(A) that PD2-31 and Dupilumab inhibit the IL-4-induced proliferation activity of the TF-1 cells with an $IC_{50}$ of 13.9 ng/ml and 21.9 ng/ml, separately. FIG. 6(B) shows the results indicating that HZD82-12 inhibits the IL-4-induced proliferation activity of the TF-1 cells. It can be seen from the results in FIG. 6(B) that HZD82-12 and Dupilumab inhibit the IL-4-induced proliferation activity of the TF-1 cells with an $IC_{50}$ of 19.3 ng/ml and 18.8 ng/ml, separately. FIG. 6(C) shows the results indicating that PD2-31 inhibits the IL-13-induced proliferation activity of the TF-1 cells. It can be seen from the results in FIG. 6(C) that PD2-31 and Dupilumab inhibit the IL-13-induced proliferation activity of the TF-1 cells with an $IC_{50}$ of 15.5 ng/ml and 20.5 ng/ml, separately. FIG. 6(D) shows the results indicating that HZD82-12 inhibits the IL-13-induced proliferation activity of the TF-1 cells. It can be seen from the results in FIG. 6(D) that HZD82-12 and Dupilumab inhibit the IL-13-induced proliferation activity of the TF-1 cells with an $IC_{50}$ of 16.1 ng/ml and 14.9 ng/ml, separately.

Figure 7A:
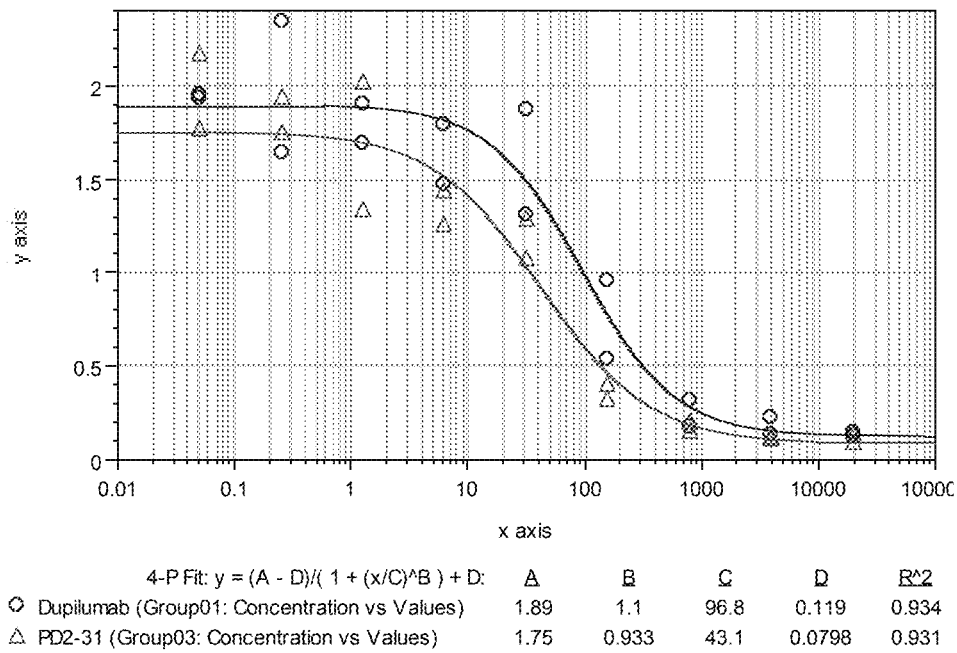
FIG. 7(A)-7(D) are graphs showing that QX005N inhibits the IL-4- or IL-13-induced CCL-11 release activity in HFL-1 cells.
Figure 7B:
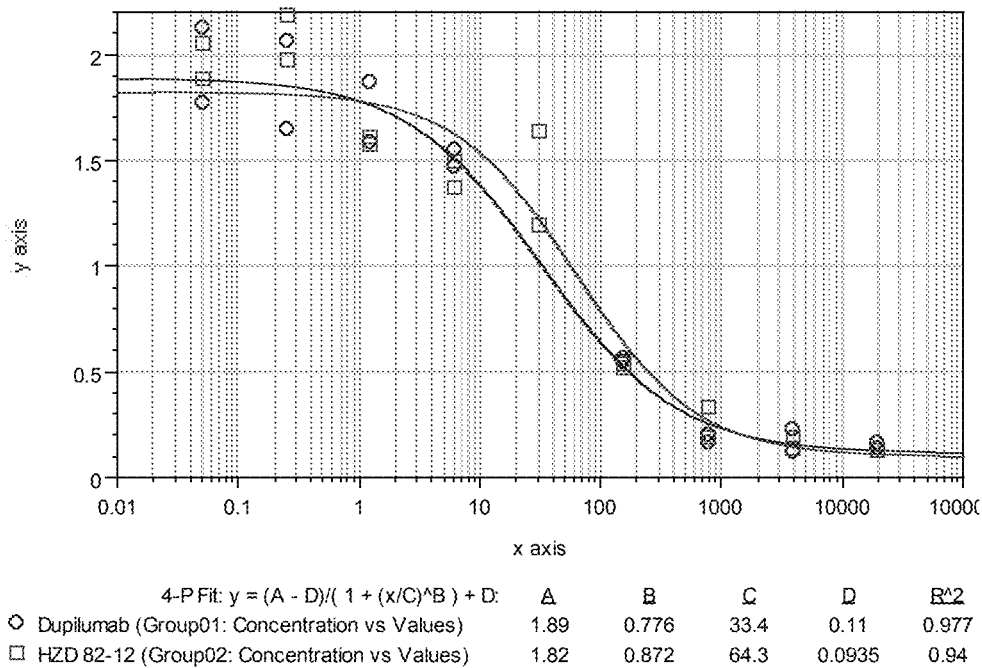
Figure 7C:
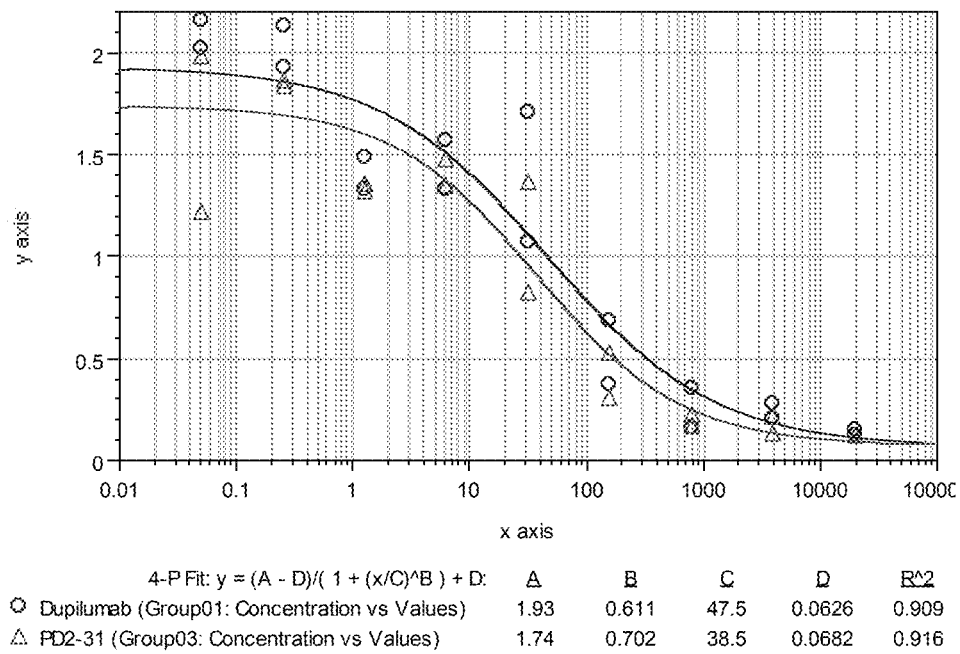
Figure 7D:
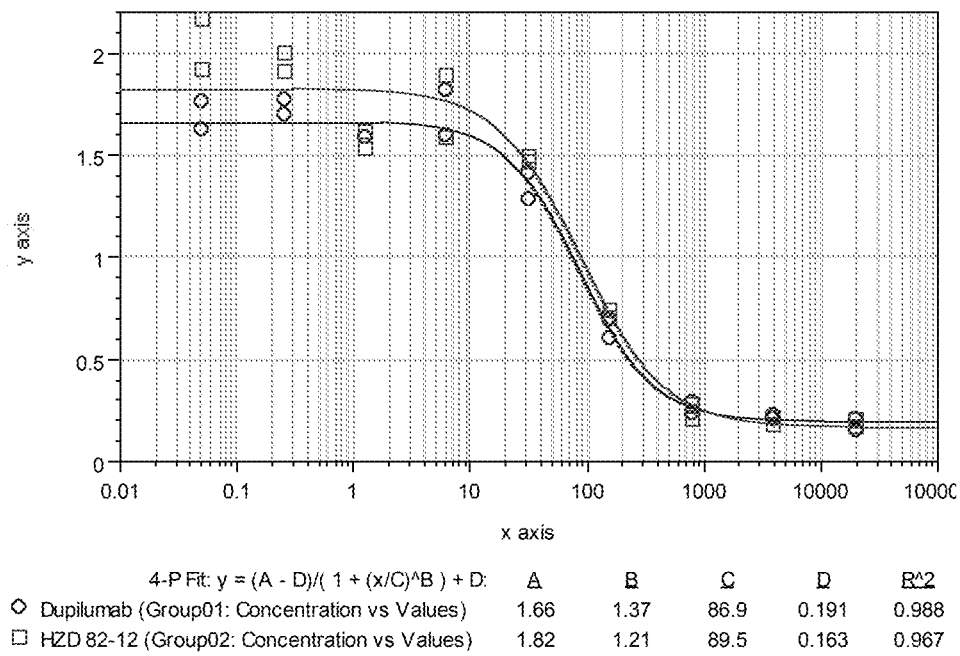

Example 8. Inhibition of the IL-4- and IL-13-Induced CCL-11 Release Activity in the HFL-1 Cells The HFL-1 human lung fibroblast cell line was used to determine the ability of PD2-31 and HZD82-12 to antagonize the CCL-11 release activity mediated by IL-4/IL-13 via IL-4Rα. The cells in culture were added to 96 wells at $4 \times 10^4$ cells per well, and then cultured overnight under the conditions of 37° C. and 5% $CO_2$. Serial dilutions with antibody concentrations ranging from 0 to 20 µg/ml were added to the cells and 20 ng/ml of TNF-α and 1 ng/ml of IL-4 or 20 ng/ml of IL-13 were added. Then, the cells were cultured for 24 hours under the conditions of 37° C. and 5% $CO_2$. The cell culture supernatant was collected. The expression of CCL-17 in the supernatant was detected by the sandwich ELISA method and the dose-response curve was plotted (FIGS. 7(A)-7(D)) to analyze the antagonistic activity of the antibody. The results show that QX005N is capable of inhibiting the IL-4/IL-13-induced CCL-11 release in the HFL-1 cells. FIG. 7(A) shows the results indicating that PD2-31 inhibits the IL-4-induced CCL-11 release activity in the HFL-1 cells. It can be seen from the results in FIG. 7(A) that PD2-31 and Dupilumab inhibit the IL-4-induced CCL-11 release activity in the HFL-1 cells with an $IC_{50}$ of 43.1 ng/ml and 96.8 ng/ml, separately. FIG. 7(B) shows the results indicating that HZD82-12 inhibits the IL-4-induced CCL-11 release activity in the HFL-1 cells. It can be seen from the results in FIG. 7(B) that HZD82-12 and Dupilumab inhibit the IL-4-induced CCL-11 release activity in the HFL-1 cells with an $IC_{50}$ of 64.3 ng/ml and 33.4 ng/ml, separately. FIG. 7(C) shows the results indicating that PD2-31 inhibits the IL-13-induced CCL-11 release activity in the HFL-1 cells. It can be seen from the results in FIG. 7(C) that PD2-31 and Dupilumab inhibit the IL-13-induced CCL-11 release activity in the HFL-1 cells with an $IC_{50}$ of 38.5 ng/ml and 47.5 ng/ml, separately. FIG. 7(D) shows the results indicating that HZD82-12 inhibits the IL-13-induced CCL-11 release activity in the HFL-1 cells. It can be seen from the results in FIG. 7(D) that HZD82-12 and Dupilumab inhibit the IL-13-induced CCL-11 release activity in the HFL-1 cells with an $IC_{50}$ of 89.5 ng/ml and 86.9 ng/ml, separately.

Figure 8A:
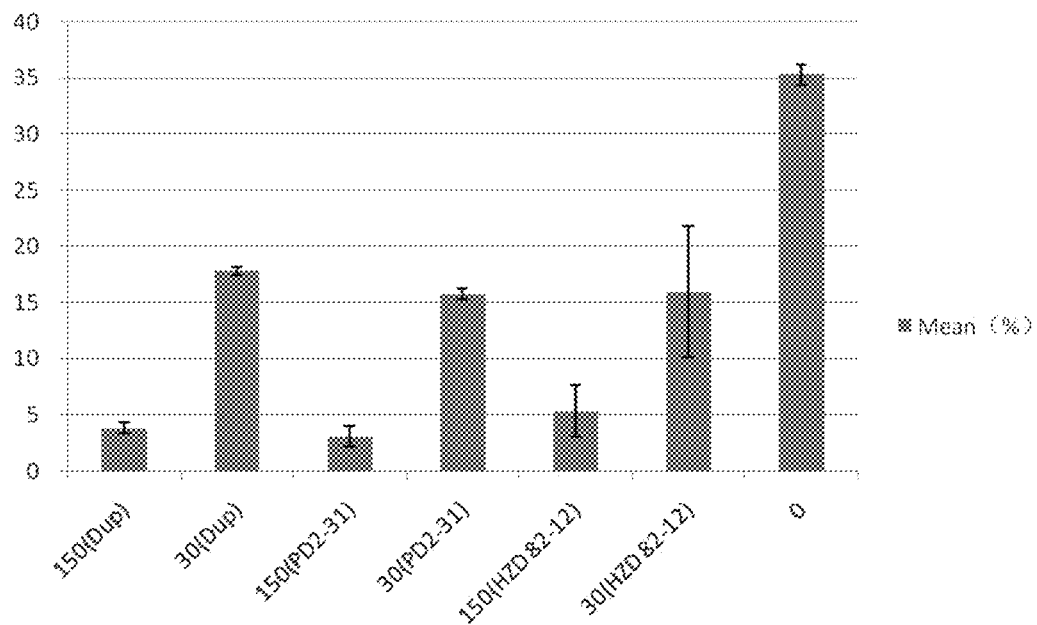
FIG. 8(A)-8(B) are graphs showing that QX005N inhibits the IL-4- or IL-13-induced CD23 expression activity in peripheral blood mononuclear cells (PBMCs).
Figure 8B:
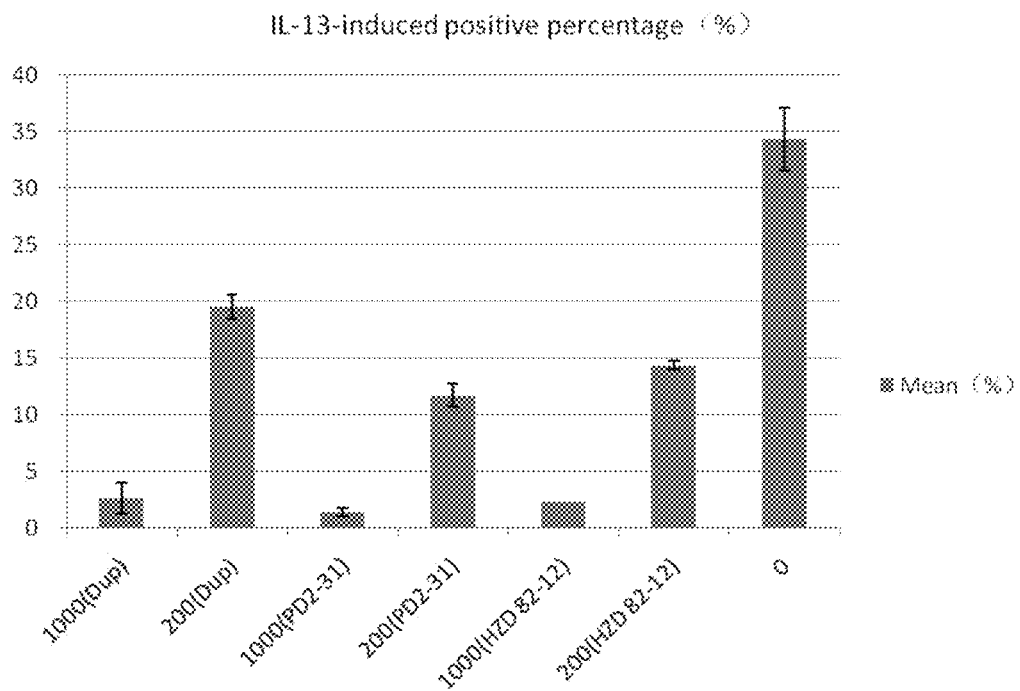

Example 9 Inhibition of the IL-4- and IL-13-Induced CD23 Expression Activity in the PBMCs The mononuclear cells isolated from human peripheral blood mononuclear cells (PBMCs) were used to determine the ability of PD2-31 and HZD82-12 to antagonize the CD23 expression activity mediated by IL-4/IL-13 via IL-4Rα. The cells in culture were added to a 24-well plate at $1.5\times10^6$ cells per well. Serial dilutions with antibody concentrations of 0, 30 ng/ml, and 150 ng/ml (for IL-4), or 0, 200 ng/ml, and 1000 ng/ml (for IL-13) were added to the cells. 1 ng/ml of IL-4 or 100 ng/ml of IL-13 was added. Then, the cells were cultured for 48 hours under the conditions of 37° C. and 5% $CO_2$. The cells were collected and the CD23 expression in the cells was detected by the FACS flow cytometry to analyze the antagonistic activity of the antibody. The results are shown in FIGS. 8(A) and 8(B), indicating that the antibodies are capable of inhibiting the IL-4- and IL-13-induced CD23 expression in the PBMCs. PD2-31 and HZD82-12 can achieve good inhibition effects at various concentrations (30 ng/ml and 150 ng/ml; or 200 ng/ml and 1000 ng/ml).

Example 10. Inhibition of the IL-4- and IL-13-Induced CCL-17 Release Activity in the PBMCs The mononuclear cells isolated from human peripheral blood mononuclear cells (PBMCs) were used to determine the ability of PD2-31 and HZD82-12 to antagonize the CCL-17 release activity mediated by IL-4/IL-13 via IL-4Rα. The cells in culture were added to 96 wells at $3\times10^5$ cells per well, and then cultured overnight under the conditions of 37° C. and 5% $CO_2$. Serial dilutions with antibody concentrations ranging from 0 to 20 μg/ml were added to the cells, and 1 ng/ml of IL-4 or 20 ng/ml of IL-13 was added. Then, the cells were cultured for 48 hours under the conditions of 37° C. and 5% $CO_2$. The cell culture supernatant was collected.

Figure 9A:
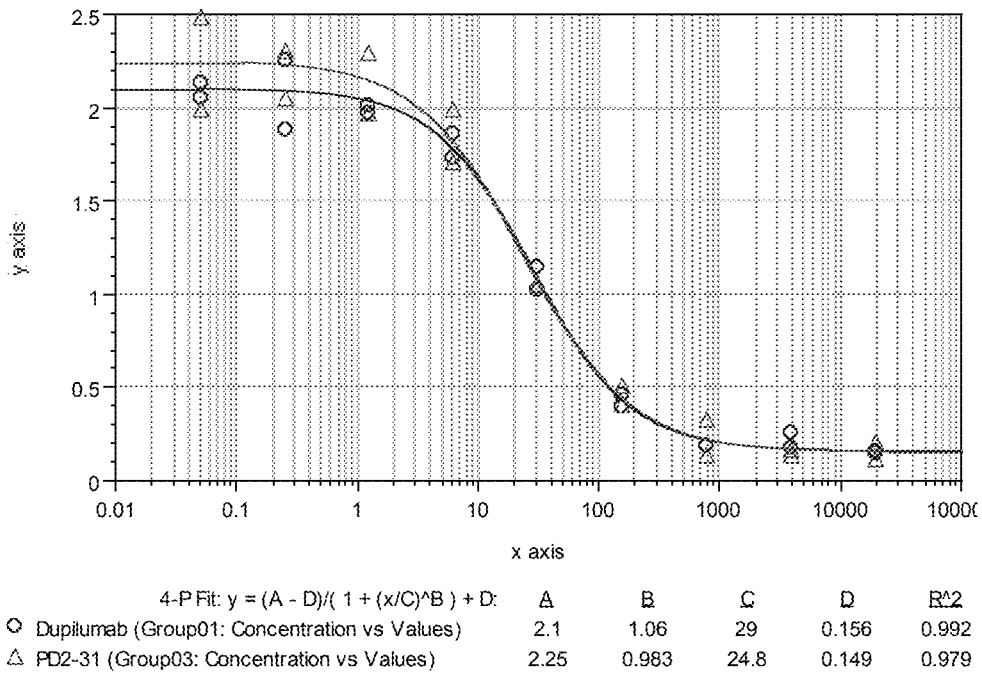
Figure 9B:
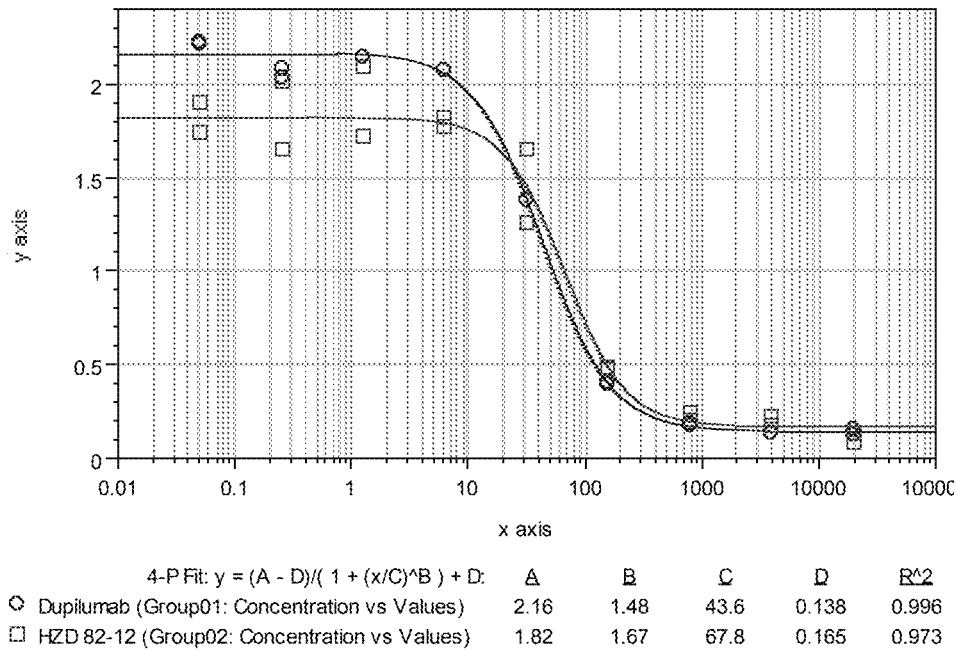
Figure 9C:
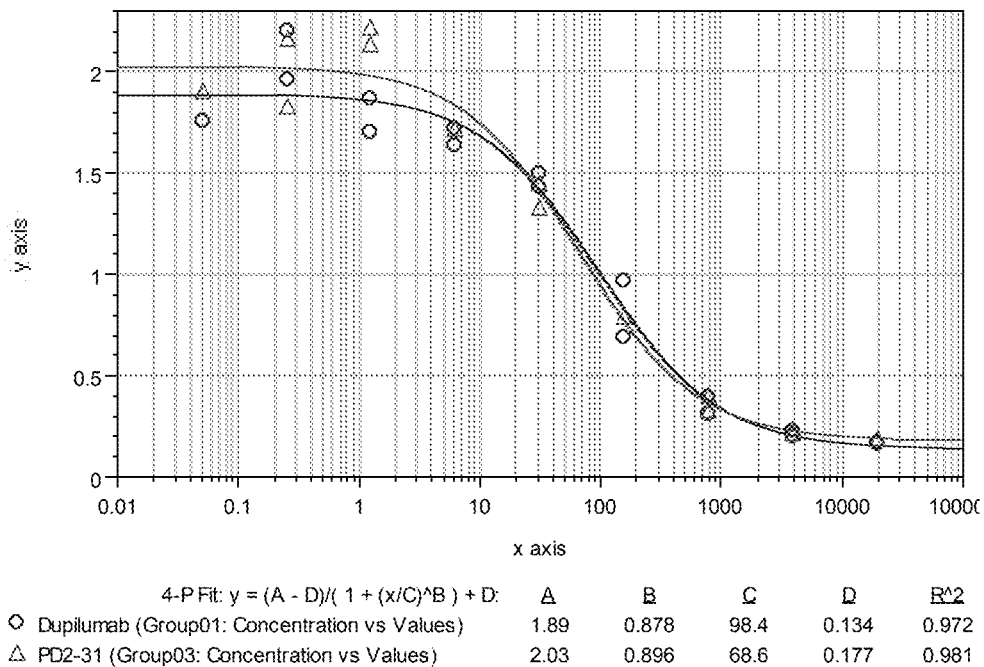

The expression of CCL-17 in the supernatant was detected by the sandwich ELISA method and the dose-response curve was plotted (FIGS. 9(A)-9(D)) to analyze the antagonistic activity of the antibody. The results show that the antibodies are capable of inhibiting the IL-4/IL-13-induced CCL-17 release in the PBMCs. FIG. 9(A) shows the results indicating that PD2-31 inhibits the IL-4-induced CCL-17 release activity in the PBMCs. It can be seen from the results in FIG. 9(A) that PD2-31 and Dupilumab inhibit the IL-4-induced CCL-17 release activity in the PBMCs with an $IC_{50}$ of 24.8 ng/ml and 29 ng/ml, separately. FIG. 9(B) shows the results indicating that HZD82-12 inhibits the IL-4-induced CCL-17 release activity in the PBMCs. It can be seen from the results in FIG. 9(B) that HZD82-12 and Dupilumab inhibit the IL-4-induced CCL-17 release activity in the PBMCs with an $IC_{50}$ of 67.8 ng/ml and 43.6 ng/ml, separately. FIG. 9(C) shows the results indicating that PD2-31 inhibits the IL-13-induced CCL-17 release activity in the PBMCs. It can be seen from the results in FIG. 9(C) that PD2-31 and Dupilumab inhibit the IL-13-induced CCL-17 release activity in the PBMCs with an $IC_{50}$ of 68.6 ng/ml and 98.4 ng/ml, separately. FIG. 9(D) shows the results indicating that HZD82-12 inhibits the IL-13-induced CCL-17 release activity in the PBMCs. It can be seen from the results in FIG. 9(D) that HZD82-12 and Dupilumab inhibit the IL-13-induced CCL-17 release activity in the PBMCs with an $IC_{50}$ of 117 ng/ml and 82 ng/ml, separately.

The results of the different assays described herein point to one or more advantages of PD2-31 compared to Dupilumab including: binding to marmoset IL-4Rα (Example 3); and showing better activity in inhibiting IL-4/IL-13 signal transduction (Example 5), inhibiting IL-4/IL-13 induced CCL-17 release in A549 cells (Example 6), inhibiting IL-4/IL-13 induced proliferation of TF-1 cells (Example 7), inhibiting IL-4/IL-13 induced CCL-11 release activity in HFL-1 cells (Example 8); and inhibiting IL-4/IL-13 CD23 expression activity in PBMCs (Example 9), and inhibiting IL-4/IL-13 induced CCL-17 release activity in PBMCs (Example 10). In addition, PD2-31 binding to a different epitope than Dupilumab, coupled with Dupilumab having a stronger $K_D$, but lower activity in different assays, suggests that PD2-31 inhibitory activity may have an additional inhibitory component compared to Dupilumab which may also offer further advantages.

The invention claimed is:

1. An antibody or fragment thereof that is either:
   a) a recombinant antibody or fragment thereof against human IL-4Rα comprising three heavy chain complementarily regions (CDR-H1, CDR-H2 and CDR-H3) and three light chain complementary determining regions (CDR-L1, CDR-L2 and CDR-L3),
   wherein the amino acid sequence of CDR-H1 is set forth in SEQ ID NO: 1, the amino acid sequence of CDR-H2 is set forth in SEQ ID NO: 2, the amino acid sequence of CDR-H3 is set forth in SEQ ID NO: 3, the amino acid sequence of CDR-L1 is set forth in SEQ ID NO: 4, the amino acid sequence of CDR-L2 is set forth in SEQ ID NO: 5, and the amino acid sequence of CDR-L3 is set forth in SEQ ID NO: 6, or
   b) a recombinant antibody or fragment thereof against human IL-4Rα comprising a heavy chain variable region comprising the amino acid sequence set forth in SEQ ID NO: 12 and a light chain variable region comprising the amino acid sequence set forth in SEQ ID NO: 13; or
   c) an isolated monoclonal antibody against human IL-4Rα comprising three heavy chain complementarily regions (CDR-H1, CDR-H2 and CDR-H3) and three light chain complementary determining regions (CDR-L1, CDR-L2 and CDR-L3),
   wherein the amino acid sequence of CDR-H1 is set forth in SEQ ID NO: 1, the amino acid sequence of CDR-H2 is set forth in SEQ ID NO: 2, the amino acid sequence of CDR-H3 is set forth in SEQ ID NO: 3, the amino acid sequence of CDR-L1 is set forth in SEQ ID NO: 4, the amino acid sequence of CDR-L2 is set forth in SEQ ID NO: 5, and the amino acid sequence of CDR-L3 is set forth in SEQ ID NO: 6, or
   d) an isolated monoclonal antibody against human IL-4Rα comprising a heavy chain variable region and a light chain variable region, wherein: the amino acid sequence of the heavy chain variable region is set forth in SEQ ID NO: 12 and the amino acid sequence of the light chain variable region is set forth in SEQ ID NO: 13.

2. The antibody or fragment thereof of claim 1, wherein said antibody or fragment thereof is said isolated monoclonal antibody.

3. The antibody or fragment thereof of claim 2, wherein said isolated monoclonal antibody c) comprises a heavy chain variable region and a light chain variable region, wherein the amino acid sequence of the heavy chain variable region is set forth in SEQ ID NO: 7 and the amino acid sequence of the light chain variable region is set forth in SEQ ID NO: 8.

4. The antibody or fragment thereof of claim 1, wherein said antibody or fragment thereof is said recombinant antibody or fragment thereof.

5. The antibody or fragment thereof of claim 4, wherein said recombinant antibody or fragment thereof is humanized.

6. The antibody or fragment thereof of claim 5, wherein said recombinant antibody or fragment thereof a) comprises a heavy chain variable region comprising the amino acid sequence set forth in SEQ ID NO: 7 and a light chain variable region comprising the sequence set forth in SEQ ID NO: 8.

7. The antibody or fragment thereof of claim 6, wherein said recombinant antibody or fragment thereof is an IgG4 antibody.

8. The antibody or fragment thereof of claim 6, wherein said recombinant antibody or fragment thereof is an antibody comprising the heavy chain amino acid sequence set forth in SEQ ID NO: 10 and the light chain amino acid is set forth in SEQ ID NO: 11; or
   wherein said recombinant antibody or fragment thereof is an antibody comprising the heavy chain amino acid sequence set forth in SEQ ID NO: 20 and the light chain amino acid sequence set forth in SEQ ID NO: 21.

9. The antibody or fragment thereof of claim 8, wherein said antibody is a monoclonal antibody.

10. An isolated nucleic acid encoding the antibody or fragment thereof of claim 1.

11. A host cell comprising the isolated nucleic acid of claim 10.

12. A pharmaceutical composition comprising the antibody or fragment of claim 1 and a pharmaceutically acceptable carrier.

13. A method of treating a disease mediated by IL-4 or IL-4/IL-13 signal transduction comprising the step of administering to a human patient in need thereof an effective amount of the antibody or fragment thereof of claim 1;

wherein said disease is selected from the group consisting of atopic dermatitis, hereditary allergic dermatitis, arthritis (including septic arthritis), chronic primary urticaria, scleroderma, hypertrophic scar, Whipple's disease, benign prostatic hyperplasia, mild, moderate and severe asthma, allergic rhinitis, chronic sinusitis, hay fever, chronic obstructive pulmonary disease, and pulmonary fibrosis, eosinophilia, psoriasis, psoriatic arthritis, and ulcerative colitis, inflammatory bowel disease, allergic reactions, Kawasaki disease, sickle cell disease, Churg-Strauss syndrome, Graves' disease, pre-eruptive purpura, Sjogren's syndrome, autoimmune lymphoproliferative syndrome, Barrett's esophagus, autoimmune uveitis, tuberculosis, and fibrosis.

14. The method of claim 13, wherein said disease is atopic dermatitis or asthma.

* * * * *